US011202798B2

(12) United States Patent (10) Patent No.: US 11,202,798 B2
Lange et al. (45) Date of Patent: Dec. 21, 2021

(54) METHOD OF TREATING OR AMELIORATING SKIN CONDITIONS WITH A MAGNETIC DIPOLE STABILIZED SOLUTION

(71) Applicant: REVEN PHARMACEUTICALS, INC., Golden, CO (US)

(72) Inventors: Peter Lange, Denver, CO (US); Brian Denomme, Northville, MI (US); Henk Van Wyk, Glendale, CO (US); Mariette Van Wyk, Glendale, CO (US); Tracy L. Krebs, Sarasota, FL (US); Sezgin Ozgur, Cary, NC (US); Zishan Haroon, Durham, NC (US)

(73) Assignee: REVEN PHARMACEUTICALS, INC., Westminster, CO (US)

( * ) Notice: Subject to any disclaimer, the term of this patent is extended or adjusted under 35 U.S.C. 154(b) by 25 days.

(21) Appl. No.: 15/848,853

(22) Filed: Dec. 20, 2017

(65) Prior Publication Data

US 2018/0243332 A1 Aug. 30, 2018

Related U.S. Application Data

(63) Continuation of application No. 15/398,233, filed on Jan. 4, 2017, now Pat. No. 9,867,849, which is a continuation of application No. 14/017,811, filed on Sep. 4, 2013, now Pat. No. 9,572,810, which is a continuation of application No. 13/811,547, filed as application No. PCT/US2011/049947 on Jul. 22, 2011, now abandoned.

(Continued)

(51) Int. Cl.
| | |
|---|---|
| *A61K 33/00* | (2006.01) |
| *A61K 33/10* | (2006.01) |
| *A23L 33/10* | (2016.01) |
| *A23L 33/15* | (2016.01) |
| *A61K 9/00* | (2006.01) |
| *A61K 9/08* | (2006.01) |
| *A61K 31/375* | (2006.01) |
| *A61K 31/4415* | (2006.01) |
| *A61K 31/519* | (2006.01) |
| *A61K 31/7036* | (2006.01) |
| *A61K 31/7048* | (2006.01) |
| *A61K 47/02* | (2006.01) |
| *A61K 47/40* | (2006.01) |
| *A61K 33/40* | (2006.01) |
| *A61K 31/197* | (2006.01) |
| *A61K 31/455* | (2006.01) |
| *A61K 31/51* | (2006.01) |
| *A61K 31/525* | (2006.01) |
| *A61K 31/714* | (2006.01) |
| *A61K 33/20* | (2006.01) |
| *A61K 8/19* | (2006.01) |
| *A61K 8/20* | (2006.01) |

(Continued)

(52) U.S. Cl.
CPC .............. *A61K 33/00* (2013.01); *A23L 33/10* (2016.08); *A23L 33/15* (2016.08); *A61K 8/19* (2013.01); *A61K 8/20* (2013.01); *A61K 8/41* (2013.01); *A61K 8/42* (2013.01); *A61K 8/67* (2013.01); *A61K 8/673* (2013.01); *A61K 8/675* (2013.01); *A61K 8/676* (2013.01); *A61K 8/73* (2013.01); *A61K 9/0019* (2013.01); *A61K 9/08* (2013.01); *A61K 31/122* (2013.01); *A61K 31/133* (2013.01); *A61K 31/167* (2013.01); *A61K 31/197* (2013.01); *A61K 31/375* (2013.01); *A61K 31/4415* (2013.01); *A61K 31/455* (2013.01); *A61K 31/465* (2013.01); *A61K 31/51* (2013.01); *A61K 31/513* (2013.01); *A61K 31/519* (2013.01); *A61K 31/525* (2013.01); *A61K 31/65* (2013.01); *A61K 31/7036* (2013.01); *A61K 31/7048* (2013.01); *A61K 31/714* (2013.01); *A61K 31/727* (2013.01); *A61K 33/12* (2013.01); *A61K 33/20* (2013.01); *A61K 33/40* (2013.01); *A61K 47/02* (2013.01); *A61K 47/14* (2013.01); *A61K 47/40* (2013.01); *A61Q 19/00* (2013.01); *A61Q 19/007* (2013.01); *A61Q 19/08* (2013.01); *A61K 2800/5922* (2013.01); *A61K 2800/78* (2013.01); *A61K 2800/805* (2013.01)

(58) Field of Classification Search
CPC ............ A61K 33/00; A61K 8/19; A23L 33/15
See application file for complete search history.

(56) References Cited

U.S. PATENT DOCUMENTS

| | | |
|---|---|---|
| 4,259,353 A | 3/1981 | Kleinberger |
| 4,837,342 A | 6/1989 | Shibasaki et al. |

(Continued)

FOREIGN PATENT DOCUMENTS

| | | |
|---|---|---|
| CN | 101717160 A | 6/2010 |
| EP | 1238945 A1 | 9/2001 |

(Continued)

OTHER PUBLICATIONS

Office Action dated Apr. 5, 2019 for U.S. Appl. No. 15/692,694.

(Continued)

*Primary Examiner* — Kyle A Purdy
(74) *Attorney, Agent, or Firm* — Volpe Koenig

(57) ABSTRACT

The present invention is directed to methods for treating or ameliorating skin conditions, diabetic conditions, cardiovascular conditions, cancer, infections or metal poisoning, enhancing performance, or providing nutritional support, comprising administering to a subject in need thereof compositions comprising a magnetic dipole stabilized solution (MDSS). The MDSS solution may include additional components and can be provided in a kit.

5 Claims, No Drawings

Related U.S. Application Data

(60) Provisional application No. 61/366,853, filed on Jul. 22, 2010, provisional application No. 61/366,852, filed on Jul. 22, 2010, provisional application No. 61/366,845, filed on Jul. 22, 2010, provisional application No. 61/366,844, filed on Jul. 22, 2010.

(51) Int. Cl.

| | | |
|---|---|---|
| *A61K 8/41* | (2006.01) | |
| *A61K 8/42* | (2006.01) | |
| *A61K 8/67* | (2006.01) | |
| *A61K 8/73* | (2006.01) | |
| *A61K 31/122* | (2006.01) | |
| *A61K 31/133* | (2006.01) | |
| *A61K 31/167* | (2006.01) | |
| *A61K 31/465* | (2006.01) | |
| *A61K 31/513* | (2006.01) | |
| *A61K 31/65* | (2006.01) | |
| *A61K 31/727* | (2006.01) | |
| *A61K 33/12* | (2006.01) | |
| *A61K 47/14* | (2017.01) | |
| *A61Q 19/00* | (2006.01) | |
| *A61Q 19/08* | (2006.01) | |

(56) References Cited

U.S. PATENT DOCUMENTS

| | | | |
|---|---|---|---|
| 5,080,886 A | 1/1992 | Mickle et al. | |
| 5,607,934 A | 3/1997 | Tone et al. | |
| 5,728,681 A * | 3/1998 | Kido | A61J 1/2093 514/23 |
| 5,736,027 A | 4/1998 | Nakamura | |
| 5,938,915 A | 8/1999 | Morisawa | |
| 6,251,259 B1 | 6/2001 | Satoh et al. | |
| 6,284,786 B1 | 9/2001 | Casciari et al. | |
| 6,344,181 B2 | 2/2002 | Boykin, Jr. | |
| 6,426,066 B1 | 7/2002 | Najafi et al. | |
| 6,506,392 B2 | 1/2003 | Siamon | |
| 6,544,401 B1 | 4/2003 | Colic | |
| 6,544,502 B2 | 4/2003 | Heesch | |
| 6,649,193 B1 | 11/2003 | Colic | |
| 6,942,767 B1 | 9/2005 | Fazzina et al. | |
| 6,968,382 B2 | 11/2005 | McBrearty et al. | |
| 7,018,623 B2 | 3/2006 | Barclay | |
| 7,374,645 B2 | 5/2008 | Davis et al. | |
| 7,691,249 B2 | 4/2010 | Daly et al. | |
| 8,367,120 B1 | 2/2013 | Norton et al. | |
| 8,455,016 B2 | 6/2013 | Norton et al. | |
| 2001/0022273 A1 | 9/2001 | Popov et al. | |
| 2001/0048915 A1 | 12/2001 | Boykin, Jr. | |
| 2002/0014460 A1 | 2/2002 | McKay | |
| 2002/0023847 A1 | 2/2002 | Natsume | |
| 2002/0027079 A1 | 3/2002 | Hanaoka | |
| 2002/0035087 A1 | 3/2002 | Barclay | |
| 2002/0158018 A1 | 10/2002 | Abramowitz et al. | |
| 2002/0160053 A1 | 10/2002 | Yahagi et al. | |
| 2002/0165220 A1 | 11/2002 | Heesch | |
| 2002/0176818 A1 | 11/2002 | Fritzberg et al. | |
| 2002/0176885 A1 | 11/2002 | Najafi et al. | |
| 2002/0179455 A1 | 12/2002 | Hanaoka | |
| 2002/0185380 A1 | 12/2002 | Hanaoka | |
| 2003/0014522 A1 | 1/2003 | McBrearty et al. | |
| 2003/0045502 A1 * | 3/2003 | Kataoka | A61K 9/0095 514/52 |
| 2003/0049163 A1 | 3/2003 | Malchesky et al. | |
| 2003/0089618 A1 | 5/2003 | Satoh et al. | |
| 2003/0105104 A1 | 6/2003 | Burzynski | |
| 2003/0175220 A1 | 9/2003 | Wang et al. | |
| 2004/0013768 A1 | 1/2004 | Khatchatrian et al. | |
| 2004/0037896 A1 | 2/2004 | Ernst | |
| 2004/0094406 A1 | 5/2004 | Sawada | |
| 2004/0110684 A1 | 6/2004 | Balligand et al. | |
| 2004/0131695 A1 | 7/2004 | Hinze | |
| 2004/0137078 A1 | 7/2004 | Najafi et al. | |
| 2005/0006592 A1 | 1/2005 | Kitada | |
| 2005/0029198 A1 | 2/2005 | Tepper et al. | |
| 2005/0037065 A1 * | 2/2005 | Kirschner | A61K 9/4858 424/456 |
| 2005/0075315 A1 | 4/2005 | Takeyama et al. | |
| 2005/0139808 A1 | 6/2005 | Alimi | |
| 2005/0175759 A1 | 8/2005 | Singhal | |
| 2005/0196462 A1 | 9/2005 | Alimi | |
| 2005/0209170 A1 | 9/2005 | Takemoto | |
| 2006/0008908 A1 | 1/2006 | Giles | |
| 2006/0065544 A1 | 3/2006 | Hanaoka | |
| 2006/0134226 A1 * | 6/2006 | Leonard | A61K 31/047 424/638 |
| 2006/0191785 A1 | 8/2006 | Ito et al. | |
| 2006/0235350 A1 | 10/2006 | Alimi et al. | |
| 2006/0263441 A1 | 11/2006 | Fukui et al. | |
| 2006/0275498 A1 | 12/2006 | Bagley | |
| 2007/0023273 A1 | 2/2007 | Kitaori et al. | |
| 2007/0148256 A1 | 6/2007 | Yanagihara et al. | |
| 2007/0166547 A1 | 7/2007 | Dobbertin et al. | |
| 2007/0173755 A1 | 7/2007 | Alimi et al. | |
| 2007/0261950 A1 | 11/2007 | Sato et al. | |
| 2008/0047844 A1 | 2/2008 | Miyashita | |
| 2008/0167345 A1 | 7/2008 | Jones et al. | |
| 2009/0214628 A1 | 8/2009 | de Rijk | |
| 2010/0316776 A1 * | 12/2010 | Miljkovic | A23L 33/125 426/271 |
| 2011/0262563 A1 | 10/2011 | Van Wyk et al. | |
| 2013/0236563 A1 | 9/2013 | Samuelson et al. | |
| 2013/0243883 A1 | 9/2013 | Norton et al. | |
| 2014/0044800 A1 | 2/2014 | Robinson et al. | |
| 2014/0050800 A1 | 2/2014 | Nieman et al. | |
| 2014/0056991 A1 | 2/2014 | Nieman et al. | |
| 2015/0093451 A1 | 4/2015 | Neiman et al. | |

FOREIGN PATENT DOCUMENTS

| | | |
|---|---|---|
| EP | 1195159 A1 | 4/2002 |
| EP | 1550637 A1 | 7/2005 |
| EP | 1721868 A1 | 11/2006 |
| JP | S5489014 | 7/1979 |
| JP | H0959150 A | 3/1997 |
| JP | 11209307 | 1/1998 |
| JP | H10272468 A1 | 10/1998 |
| JP | 2000033377 A | 2/2000 |
| JP | 2003340453 A | 12/2003 |
| JP | 20048973 | 1/2004 |
| JP | 2006098003 A | 4/2006 |
| JP | 2007253131 | 10/2007 |
| JP | 6348942 B2 | 6/2018 |
| WO | 00/71476 A1 | 11/2000 |
| WO | 01/19365 A1 | 3/2001 |
| WO | 200189520 A2 | 11/2001 |
| WO | 02/069955 A1 | 9/2002 |
| WO | 03/037802 A1 | 5/2003 |
| WO | 03/050044 A1 | 6/2003 |
| WO | 2005/044176 A2 | 5/2005 |
| WO | 2006/025563 A1 | 3/2006 |
| WO | 2006/035523 A1 | 4/2006 |
| WO | 2006/098405 A1 | 9/2006 |
| WO | 2006/102681 A2 | 9/2006 |
| WO | 2006/107760 A1 | 10/2006 |
| WO | 2007/072147 A2 | 6/2007 |
| WO | 2007051431 A3 | 6/2007 |
| WO | 2007/140544 A1 | 12/2007 |
| WO | 2008/041031 A1 | 4/2008 |
| WO | 2010/011927 A1 | 1/2010 |
| WO | 2011/085316 A1 | 7/2011 |
| WO | 2015107731 A1 | 7/2015 |

OTHER PUBLICATIONS

Australian Office Action dated Jun. 1, 2018 for the Australian Patent Application No. 2016200103.

(56) References Cited

OTHER PUBLICATIONS

Desai, et al. "The Efficacy and Tolerability of Electrolyzed Oxidized Water in Treating Mild to Moderate Acne", Cosmetic Dermatology, Feb. 2004, vol. 17, No. 2, pp. 93-105.
Lenfant (Biomedicine & Pharmacotherapy 58 (2004) 248-254).
Bisla et al., "Concentration-Dependent Effects of Lidocaine on Corneal Epithelial Wound Healing," Investigative Ophthalmology and Visual Science, vol. 33, No. 11, pp. 3029-3033 (Oct. 1992).
Hsu, "Effects of flow rate, temperature and salt concentration on chemical and physical properties of electrolyzed oxidizing water," Journal of Food Engineering 66, pp. 171-176 (2005).
USPTO STIC structure search for Claim 2 of U.S. Appl. No. 13/055,691.
Martinez-Huitle et al., "Electrochemical Alternatives for Drinking Water Disinfection," Chem Int Ed Engl. 47(11), pp. 1998-2005 (2008).
Erickson et al., "Inactivation of Protozoan Parasites in Food, Water, and Environmental Systems," J Food Prot. 69(11), pp. 2786-2808 (Nov. 2006).
Kerwick et al., "A Methodology for the Evaluation of Disinfection Technologies," J Water Health. 3(4), pp. 393-404 (Dec. 2005).
Feng et al., "Water Disinfection by Electrochemical Treatment," Bioresour Technol. 94(1), pp. 21-25 (Aug. 2004).
Avchinnikov, "Sanitary Assessment of Currently Available Methods of Drinking Water Disinfection (Review)," Gig Sanit. (2), pp. 11-20 (Mar.-Apr. 2001). (English abstract provided).
Okochi et al., "Electrochemical Disinfection of Drinking Water Using an Activated-Carbon-Fiber Reactor Capable of Monitoring its Microbial Fouling," Appl Microbiol Biotechnol. 47(1):18-22 (Jan. 1997).
Feedlyte, http://www.distrilyte.com/index.php?page=4 (Nov. 6, 2007).
Envyrolyte, http://www.envirolyte.com/group.shtml (Mar. 17, 2009).
Envirocleanse, LLC, http://www..eco-enviro.com (Nov. 20, 2008).
Health Homes Plus, http://www.healthyhomesplus.com/articles/anolyte_water.htm (Jan. 19, 2010).
Hambidge A. "Reviewing Efficacy of Alternative Water Treatment Techniques—Part 2"; Health Estate. Aug. 2001; 55(7):24-6.
D. Frumkin et al.: "Authentication of forensic DNA samples", Forensic Sci. Int. Genet. Sep. 20, 2001 (Sep. 20, 2001), XP26829808.
D. Frumkin et al.: "DNA-methylation-based forensic tissue identification", Forensic Sci. Int. Genet. vol. 5, No. 5, Dec. 6, 2010 (Dec. 6, 2010), pp. 517-524, XP028275689.
USPTO STIC Structure Search for Claim 2 of U.S. Appl. No. 14/550,677 (2015).
Communication (Supplementary EP Search Report) in EP Appln. No. 11 81 0437 dated Dec. 12, 2013.
International Search Report in PCT/US2011/44947 dated Feb. 29, 2012.
International Search Report for PCT/US2009/051694.
International Preliminary Report on Patentability for PCT/US2009/051694.
Office Action for Japanese Application No. 2016189741.
Konnichi no Chiryouyaku "Today's therapeutic agents" {2003 version), Nankodo Co., Ltd., pp. 388, 396, 398-399, 414-415,418-419,433,468-469,925, and 930.
Xie, Minkang, "The effects of the application of electroactivated water in the healthy treatment of poultry meat workshop appliances," Guide to Chinese Poultry, (Publ. Dec. 31, 2000) vol. 17, No. 17, p. 20.
"Antibiotics can reduce the occurrence of cardiovascular events," Henan Medical Research, vol. 11, p. 192, publication date: Jun. 30, 2002.
Mulder, J. et al. "Intermittent Intravenous Lidocaine for the Treatment of Wound Pain" (2010) Journal of Pain and Symptom Management 39(2):339-340.
Heyman et al., "9-Cis Retinoic Acid Is a High Affinity Ligand for the Retinoid X Receptor," Cell (Jan. 24, 1992); 68:397-406.
Marklund, et al: "Normal CuZn Superoxide Dismutase, Mn Superoxide Dismutase, Catalase and Glutathione Peroxidase in Werner's Syndrome", Journal of Gerontology, 1981, vol. 36, No. 4, pp. 405-409.
Guaiquil, et al: "Vitamin C Inhibits Hypoxia-Induced Damage and Apoptotic Signaling Pathways in Cardiomyocytes and Ischemic Hearts", Free Radical Biology & Medicine, 2004, vol. 37, No. 9, pp. 1419-1429.
Violi, et al: "Vitamins E and C for Prevention of Cardiovascular Disease", Current Development in Atherosclerosis Research, 2006, 117-114, Nova Science Publishers, Inc. (abstract).
Takami, A. et al. "Successful therapy of myelodysplastic syndrome with menatetrenone, a vitamin K2 analog" (1999) Int J Hematol 69(1):24 26.
Today's Therapeutic Drugs (2003 Edition), Nankodo, Co. Ltd., 2003, p. 388, 396, 398-399, 414-415, 418-419, 433, 468-469, 925, and 930.
Office Action for Brazilian Patent Application No. 1120130015942, dated Jul. 13, 2021.
Office Action for Japanese Patent Application No. 2018-105762, dated Sep. 15, 2021.

\* cited by examiner

METHOD OF TREATING OR AMELIORATING SKIN CONDITIONS WITH A MAGNETIC DIPOLE STABILIZED SOLUTION

CROSS REFERENCE TO RELATED APPLICATION

This application is a continuation of U.S. patent application Ser. No. 15/398,233, which was filed Jan. 4, 2017 and is a continuation of U.S. patent application Ser. No. 14/017,811, which was filed Sep. 4, 2013 and was a continuation of U.S. patent application Ser. No. 13/811,547, which is now abandoned and was a 371 of PCT/US2011/044947, which was filed Jul. 22, 2011 and claimed the benefit of U.S. Provisional Patent Application No. 61/366,853, filed Jul. 22, 2010, U.S. Provisional Patent Application No. 61/366,852, filed Jul. 22, 2010, U.S. Provisional Patent Application No. 61/366,845, filed Jul. 22, 2010, and U.S. Provisional Patent Application No. 61/366,844, filed Jul. 22, 2010, all of which are incorporated herein by reference as if fully set forth herein.

FIELD OF THE INVENTION

The present invention is directed to methods involving the administration of a composition comprising a magnetic dipole stabilized solution to a subject in need thereof for treating or ameliorating skin conditions, diabetic conditions, cardiovascular conditions, cancer and infections, chelating, reducing the amount of metal in a subject or increasing the amount of excretion of metal from a subject, providing nutritional support or enhancing performance.

BACKGROUND

A magnetic dipole stabilized solution which can be an electro-activated water is sterile and non-pyrogenic and is produced by exposing the water to a strong electrical (magnetic) field force in a tightly isolated and fully enclosed reactor space. It is capable of producing both a negative (cathodic) and a positive (anodic) stream of activated water.

Electrolysis of water, including saline solutions, is known for antimicrobial properties and for use on hard surfaces (U.S. Pat. Nos. 4,236,992 and 4,316,787). Electrolyzed water has been administered for therapeutic use through ingestion or topical administration. Published U.S. Patent Application No. 20060008908 discloses a beverage containing electrolyzed water and a cesium or rubidium salt for promoting longevity. The application notes that there may be an electro-physiological imbalance that is the origin of disease and that electrolyzed water can restore optimal pH. The electrolyzed water is disclosed as an alkaline water. Published U.S. Patent Application No. 20050074421 discloses an acidic electrolyzed water composition. It is for external use and is purported to be a cosmetic and a hair growing tonic. An electrolyzed water composition is disclosed in U.S. Pat. No. 6,544,502. An antibiotic can be admixed in the water and used topically to treat acne. An electrolyzed saline solution containing regulated amounts of ozone and active chlorine species is described in U.S. Pat. No. 5,622,848. The solution can be given intravenously.

Cardiovascular diseases, which include coronary heart disease (heart attacks), cerebrovascular disease, raised blood pressure (hypertension), peripheral artery disease, rheumatic heart disease, congenital heart disease and heart failure, derive from dysfunctional conditions of the heart, arteries, and veins that supply oxygen to vital life-sustaining organs, including the brain and the heart itself. Major causes of cardiovascular disease are tobacco use, physical inactivity and an unhealthy diet.

Heart attacks and strokes are mainly caused by a blockage in the inner walls of the blood vessels that prevents blood from flowing to the heart or the brain. Arteriosclerosis and atherosclerosis are excess buildup of fat or plaque deposits, respectively, that cause narrowing of the veins that supply oxygenated blood to the heart and may lead to ischemic heart disease, an obstruction of blood flow to the heart. Excess fat or plaque buildup may also cause high blood pressure (hypertension), a disease known as "The Silent Killer" because the first warning sign is an angina attack, a deadly heart attack or a stroke. Kidney disorders, obesity, diabetes, smoking, excess alcohol, stress, and thyroid and adrenal gland problems can also exacerbate a high blood pressure condition.

Damage to the heart tissues from cardiovascular diseases or heart surgery disrupts the natural electrical impulses of the heart and results in cardiac arrhythmia. Sudden fluctuations in heart rate can cause cardiac irregularities and insufficiencies, including palpitations, supraventricular tachycardia, fibrillation faintness or dizziness, and even initiate a heart attack. Mismatch of cardiac output during strenuous exercise may lead to muscle damage, induce fatigue and affect athletic performance. Arteries spasm and irregular contraction and expansion of blood vessels in the brain may reduce flow of blood from the occipital lobe and trigger migraines. Levels of total blood cholesterol above 250 mg/dL, LDL cholesterol above 130 mg/dL (3.0 mmol/L), HDL cholesterol below 35 mg/dL and lipoprotein(a) level greater than 30 mg/dL may also lead to a heart attack or stroke.

Infections of the heart, known as carditis and endocarditis, may occur as a result of a weak immune system, liver problems, heart surgery, or from an autoimmune disorder like rheumatic fever.

Heavy smoking may cause Buerger's disease, also known as thrombophlebitis obliterans, an acute inflammation and thrombosis (clotting) of arteries and veins of the hands and feet, which is often associated with intense pain in the extremities, claudication in the feet and/or hands, numbness and/or tingling in the limbs, skin ulcerations, gangrene and Raynaud's phenomenon, a condition in which the distal extremities turn white upon exposure to cold.

Peripheral arterial occlusive disease may cause diabetic ulcers, which are the most common foot injuries leading to lower extremity amputation in diabetic patients.

Research indicates the course of events which leads to the loss of function, deterioration, destruction and death of the human cell and to a large extent research relates to the issue of human cellular reliance on oxygen metabolism, which occurs intracellularly. Oxygen uptake intracellularly is governed by the metabolic need for energy and takes place within the mitochondria to produce ATP, the cell's energy source. Such chemical reactions are not 100% efficient and the resultant release of highly reactive oxygen species cytoplasm is responsible for cellular damage. The relative amount of such oxygen by-products is less than the amount produced in many other mammal species, however, such by-products are highly toxic. Such examples include superoxide and hydroxyl radicals, which can cause oxidative damage to cells and tissues. Superoxide and water produce concentrated hydrogen peroxide and is capable of intense skin damage within a few seconds, when applied to human skin. The same reaction occurs intracellularly within the cytoplasm and causes severe damage. The cells are protected by means of enzymes to destroy peroxide radicals continually, however, such defenses are not 100% efficient with the result that chemical destruction of cells occurs.

Free oxygen radicals, also known as reactive oxygen species (ROS), cause much damage to macromolecules, including lipids, proteins and nucleic acids. One major toxic effect of oxygen radicals is damage to cellular membranes, including the plasma, mitochondrial and endo-membrane systems, which is initiated by lipid peroxidation and is accompanied by increased membrane rigidity, decreased activity of membrane-bound enzymes, altered activity of membrane receptors and altered membrane permeability. Furthermore, oxygen radicals can also directly attack membrane proteins and induce lipid-lipid, lipid-protein and protein-protein crosslinking, which in turn affects membrane function.

Because of their reactivity, free oxygen radicals may react with DNA, resulting in mutations that can adversely affect the cell cycle and potentially lead to cancer and malignancies. Moreover, oxygen free radicals are involved in cardiovascular diseases, the aging process, neurodegenerative diseases, including ALS, Parkinson's disease and Alzheimer's disease, cataractogenesis, atherosclerosis, diabetes mellitus, ischemia-reperfusion injury, kwashiorkor, senile- and drug-induced deafness, schizophrenia, atherosclerosis and alcohol-induced liver damage.

There is strong evidence in the literature that free oxygen radicals oxidize low density lipoprotein (LDL), which is then engulfed by phagocytes to form foam cells and plaques in the cardiovascular wall. These plaques harden and narrow the blood vessels and impair blood flow, thus depriving the heart of oxygen and nutrients. In addition, ischemia is often followed by reperfusion injury, which is caused by inadequate supplies of intracellular antioxidants. Ischemia and reperfusion are a major cause of strokes. There is also increasing evidence that mismatch of cardiac output during strenuous exercise causes release of free oxygen radicals, which contribute to muscle damage and induce fatigue and/or injury. Moreover, it has been reported that the activity of the anti-oxidant enzymes superoxide dismutase (SOD), catalase (CAT) and glutathione peroxidase (GSH-Px) is significantly lower in subjects suffering from migraine. SOD is known to protect against vasoconstriction or vasospasm induced by superoxide radicals. Migraine is a potential risk factor or marker for atherosclerosis-related diseases.

An example of cell damage caused by oxygen reactions is damage to the DNA. It is evident that DNA destructive reactions occur daily in normal man. Most of these are repaired enzymatically, if not, such cells reproduce out of control, with resulting neoplasms. However, the long-term aging effects of endogenous damage, is exemplified by wrinkling and hardening of the skin and arteries with age. Skin and arteries consist of collagen and elastin tissue. Collagen is the major protein of white fibers of the body's connective tissues, cartilage and bone. Elastin is the major connective tissue of structures such as large blood vessels and skin. It is elastin that enables these structures to stretch and resume to original size and shape. Free radical changes described above yields a pathology, which leads to neoplastic changes, atherosclerosis and loss of elasticity of the skin. The pathology is centered on the cell membranes in all organs and affected by the supply of nutrients, vitamins, and nucleic acids through the microcirculation. Recent scientific studies have shown that this mechanism progresses from free radical reactions to oxidative products, which damages cells and tissues. This simultaneously affects all cells, tissues and organs throughout the body and is progressively insidious. These processes involve a fundamental aspect of homeostasis and cell physiology.

The clinical significance of the chemical damage generated in living cells, has been documented. It is therefore necessary to develop methods to inhibit damage caused by these mechanisms.

Circulation disorders are common disorders amongst the populace. It may be a severe medical challenge and may lead to limb loss and a marked reduction in quality of life. Circulation disorders are often diagnosed at a late stage of the disease. Non-healing small wounds are the early characteristics of poor circulation. Such wounds are often treated without the underlying cause being correctly diagnosed. This results in ulceration, discomfort and pain and may lead to limb amputation. Poor circulation can also manifest itself in a patient being able to only walk short distances, and be the cause of severe cramps. Other examples are patients with no feeling in their toes and or feet and severe discoloration of either the hand or foot.

A general condition has been identified in this disease as being part of an autoimmune syndrome manifesting as a general inflammatory condition of the vascular system, more specifically vasculitis. Vasculitis may be considered an inflammatory syndrome with structural alterations of the vascular wall, complicated by lumen occlusion, leading to tissue ischemia. Vessels of any size may be altered in systemic vasculitis but in cutaneous forms alteration affects small vessels, especially those post-capillary. The various forms differ by age of onset, affected organ, and presence of periods of remission and exacerbation, amongst other features. Sometimes they may also be superimposed to other well-defined diseases, as vascular disorders, identified as secondary conditions such as neoplasia, allergic reactions, and infections.

Infections can promote inflammation of the vascular intima wall of any diameter and in any organ. Palpable purpura is the most common manifestation of vasculitis, although erythematous macules, nodule, ecchimoses, erosions, ulcerations, hemorrhagic blisters, necrosis, and gangrene may also occur. Skin can be the target organ in this type of vascular pathology. The relative frequency of vasculitis of the skin may be the first manifestation of a very severe systemic disease.

Relative and or absolute ischemia caused by vascular disease such as sclerosis resulting from aging, results in compromised poor blood flow to tissues and cells. This results in a lack of nutrients and oxygen at cellular level from reaching the cells, with the resulting symptoms of ageing. This is manifested by such symptoms as a loss of mental agility, alertness, memory loss and other conditions commonly seen in senescence. In normal metabolism most of the metabolic energy is used to maintain gradients across the cell membrane. The provision of nutrient substrates is recognized as the best basis for maintaining a level of metabolic activity and ongoing energy needs in the cell. In these instances diseases as manifested by neurodegeneration of aging may also be modulated. Because neuron function can be disrupted by many substances in the blood, it is necessary to target the central nervous system by means of carrier fluids capable of breaching the blood brain barrier by introducing charged and or lipid substances into the blood may accomplish this. It is known that chemical communication in the brain may be influenced by norepinephrine, acetylcholine, serotonin, endorphin and many other naturally occurring chemicals in the brain.

The effects of aging may be attributed, on a molecular level, to the oxidative processes in the cell which is harmful to proteins, lipids and nucleic acids. By providing sufficient anti-oxidants, it may be possible to modulate or even reverse the effects of aging at molecular level. Biological aging processes are part of the increase in disorder at cellular level with the acknowledged difference being that in the case of a pathological multi-system, atrophy or senescence at cellular level, multi-organ failure may occur. This process is demonstrated by reduction in cellular mass of the organs and may be seen in the aged on autopsy. For instance, the human brain can decrease from an average weight of 1500 grams to less than 1000 grams in advanced age.

The senescent organ loses many functions, leading to premature aging, for instance the brain loses its memory retention capability, cannot react quickly to external stimuli and is unable to memorize new information. Loss of mass is also demonstrated in organs such as the liver, kidneys, lymph nodes, skeletal muscle and bones. Corresponding changes are seen in depleted fat deposits, skin elasticity, brittle bones, low resistance to infection, lack of exercise tolerance and reproductive ability. At the cellular level, aging means inadequate DNA repair, leading to disorder in cell replication Loss of mitosis in the nucleus of the cell, followed by a closing of the microcirculation. This results in so-called cell drop-out and loss of organs, as well as membrane function, in particular the TNP or transmembrane potential. This process is progressive and affects all organs and tissues throughout the body. The etiology and pathogenesis of this condition involves a universal and fundamental aspect of cell physiology.

In any study on aging, two distinct types of cells must be considered. These include normally dividing cells and post-mitotic cells, normally dividing cells are those of the skin, hair and gastrointestinal tract. Thousands of such cells die daily, but are continually replaced with exact replicas until the time of aging begins. This begins in the mid-twenties in humans. The second cell type is that which makes up the central nervous system, brain and heart. In general, post-mitotic cells do not divide or reproduce. Humans are born with a fixed number of post-mitotic cells, which lose function and die daily throughout the human life span. Death, as a result of aging, occurs when a critical number of post-mitotic cells lose function within a critical organ, such as the brain.

Congenital defects and infectious disease can strike anywhere. One of the most common diseases occurs in the arteries: atherosclerosis. Blockages can occur in veins as well as in arteries, but these tend to be caused by blood clots, or thrombi, rather than by atherosclerosis. Thrombophlebitis (or often called phlebitis) most commonly involves clotting of blood and inflammation of a vein in the leg. This can be serious if a portion of the clot becomes detached, travels through the heart and gets pumped to the lung where it blocks a pulmonary artery as a pulmonary embolism. About 10% of people with pulmonary embolism die within an hour. Clotting of blood in the veins can occur when blood flow is slow or stagnant. This can occur during long periods of immobilization such as when a person is confined to a hospital bed, cramped in a crowded airplane on a long flight or driving for an extended period.

Atherosclerosis (hardening of the arteries) occurs "naturally" with aging as a result of cross-linking of macromolecules like proteins and polysaccharides. Atherosclerosis refers to the formation and hardening of fatty plaques (atheromas) of the inner surface of the arteries. In atherosclerosis, the arteries not only harden, they narrow, sometimes narrowing so much that hardly any blood can get through. Such narrows vessels are easily blocked by constriction or objects in the bloodstream.

The internal surface of an artery is covered with a single layer of endothelial cells that are pressed against each other like flagstones on a terrace. Atherosclerosis begins with injury to endothelial cells, exposing portions of the artery surface below the endothelium. Free radicals, chemicals in cigarette smoke or other irritants could be responsible for the injury, as could turbulence and mechanical force due to high blood pressure. Platelets (round cells half as large as red blood cells) clump around the injured endothelial cells and release prostaglandins, which cause the endothelial cells to proliferate like cancer. LDL-cholesterol particles release their fat into the areas made porous by prostaglandins. Macrophages (scavenger white blood cells) engorge themselves on oxidized LDL-cholesterol until they become unrecognizable "foam cells" that invade atheromas. Then the atheromas are hardened by fibrin (which forms scar tissue) and finally by calcium patches. A vicious circle often arises with scar tissue attracting more platelets and LDL-engorged macrophages. Atherosclerosis can occur in any artery. Most commonly it occurs in the aorta, the artery that receives blood directly from the heart. Since the aorta is the largest artery in the body, it is rarely critically narrowed by atheromas. Nonetheless, atherosclerosis can contribute to aneurysms (ballooning of an artery, responsible for only one-fortieth of the mortality rate of heart attack—an aortic aneurysm killed Albert Einstein, who refused to be operated upon.) The most frequent life-threatening problems, however, are caused by the arteries supplying the heart, the brain and the kidneys, in that order.

Since the blood is 80% water, fats will not dissolve in the blood. Therefore, fats need to be attached to carrier molecules to travel through the bloodstream. The principle carrier molecules for fat are albumin, chylomicrons, Very Low Density Lipoprotein (VLDL), Low Density Lipoprotein (LDL) and High Density Lipoprotein (HDL). Free Fatty Acids (FFAs) are attached to albumin, whereas triglycerides are mainly transported by chylomicrons and VLDL. Cholesterol and phospholipid are primarily transported by LDL and HDL. Cholesterol is supplied to cells primarily by the attachment of LDL to specific LDL receptors on cell membranes. Thyroid hormone lowers blood cholesterol by increasing the number of LDL receptors on cells. For most people, atherosclerosis due to excessive LDL-cholesterol in the blood is the result of a high level of dietary saturated fat resulting in high LDL-cholesterol production by the liver. The primary function of HDL seems to be to remove excess cholesterol from the bloodstream. LDL can directly release cholesterol into arterial areas made porous by prostaglandins—whereas HDL can scoop up this loose cholesterol and return it to the liver. Thus, HDL deficiency can be as serious an atherosclerosis risk as LDL-cholesterol excess. A 1% reduction in blood cholesterol is generally associated with a 2% reduction in risk of coronary artery disease, within "normal" levels of blood cholesterol.

Free fatty acids are a major source of energy for many organs, including the heart. Triglycerides are hydrolyzed into FFAs and glycerol by the enzyme lipase, which is found both inside cells and on the surface of the endothelial cells of capillaries. Phospholipid is an essential constituent of cell membranes. Cholesterol is also an essential constituent of cell membranes, particularly in the nervous system. Cholesterol is also the principle precursor of cortisone and sex hormones. 93% of cholesterol is found in cells and only 7% in plasma.

The coronary calcium scan is a test that assists in showing whether a patient is at risk of developing a coronary artery disease (CAD), by determining the presence of plaque (fatty deposits) in blood vessels. The presence and amount of calcium detected in a coronary artery indicates the presence and amount of atherosclerotic plaque. Since calcium deposits appear years before the development of heart disease symptoms such as chest pain and shortness of breath, a coronary calcium scan is most useful for people who are at moderate risk of having a heart attack within the next 10 years, and may help doctors decide whether a patient needs treatment. The calcified plaque burden caused by calcium deposits is measured with the Calcium Score, also called the Agatston Calcium Score, which is computed for each of the coronary arteries based upon the volume and density of the calcium deposits. The calcified plaque burden does not correspond directly to the percentage of narrowing in the artery but does correlate with the severity of the underlying coronary atherosclerosis. The score is then used to determine the calcium percentile, which compares the calcified plaque burden in a subject to the calcified plaque burden in other asymptomatic men and women of the same age. The calcium score, in combination with the percentile, enables the physician to determine the risk of developing symptomatic coronary artery disease and to measure the progression of disease and the effectiveness of treatment.

A score of zero indicates the absence of calcified plaque burden and significant coronary artery narrowing, although it does not entirely rule out the presence of soft, non-calcified plaque or the possibility of a cardiac event. A subject with a score of zero has a very low likelihood of a cardiac event over at least the next 3 years. A score greater than zero indicates at least some coronary artery disease. As the score increases, so does the likelihood of a significant coronary narrowing and coronary event over the next 3 years, compared to people with lower scores. Similarly, the likelihood of a coronary event increases with increasing calcium percentiles.

Often, there are no symptoms of underlying cardiovascular diseases and a heart attack or stroke may be the first warning. Early medical detection and treatment is available, however, is not always effective. Angiograms, bypass surgery and angioplasty are invasive and traumatic procedures associated with high cost and often requiring additional therapy and/or intervention.

The use of chelating agents of various types to entrap metal ions useful in magnetic resonance imaging is well known. Generally, the chelating agents contain a substantial number of unshared electron pairs or negatively charged or potentially negatively charged species. Perhaps the simplest among these is ethylenediaminetetraacetic acid (EDTA) commonly used as a water softener. However, many such agents are known, including, most notably, and commonly used, diethylene triamine pentaacetic acid (DTPA) and tetraazacyclododecanetetraacetic acid (DOTA) and their derivatives. U.S. Pat. Nos. 5,573,752 and 6,056,939, disclose derivatives of DOTA which are coupled to a benzyl or phenyl moiety wherein the phenyl ring is substituted by isothiocyanate. This isothiocyanate provides a reactive group for coupling to various additional compounds. As described in these patents, the isothiocyanate group can be used to couple the chelate to a targeting agent such as an antibody or fragment thereof.

However, many conditions and diseases are brought on by damage at the cellular and intracellular level. Often the mechanisms for cellular repair are inadequate or so compromised the cells cannot recover or the mechanisms that cause the damage simply overwhelm the cell. The clinical significance of the damage generated in living cells is manifested in a diseased cell or symptoms of an underlying condition. It would be beneficial to develop methods to facilitate the inhibition of cellular damage or boost recovery. The presently disclosed subject matter addresses, in whole or in part, these and other needs in the art.

SUMMARY

It is therefore an object of the invention to provide solutions to the aforementioned needs.

To this end, the invention provides methods of treating or ameliorating skin conditions, diabetic conditions, cardiovascular conditions, cancer or infections by administering a magnetic dipole stabilized solution (MDSS) are provided. Also provided are methods of chelating, reducing the amount of metal in a subject, increasing the amount of excretion of metal from a subject, enhancing performance and nutritional supplementation by administering a magnetic dipole stabilized solution (MDSS). Thus, in one embodiment, the present invention provides a method of treating or ameliorating a skin condition, a condition associated with diabetes, a condition associated with a cardiovascular dysfunction, a cancer, an infection or metal poisoning in a subject in need thereof comprising administering to the subject by injection a therapeutically effective amount of a composition comprising a magnetic dipole stabilized solution. Preferably, the magnetic dipole stabilized solution is an electroactivated water having a negative electrical potential of about −990 to about −0.0001 mV, and comprising stabilized oxidative species selected from the group consisting of $H_2O$, $O_2$, $H_2O_2$, $Cl_2O$ and $H_3O$. In one aspect of the invention, the skin condition is skin aging, wrinkles, acne, photodamage, rosacea, scars, eczema, alopecia, hypertrophic scars, keliods, stretch marks or Striae distensae, psoriasis, pruritus, ehlers-danlos syndrome, scleroderma, post inflammatory hyperpigmentation, melasma, alopecia, poikiloderma of civatte, vitelligo, skin cancers, skin dyschromas, burns or blotchy pigmentation. In a preferred aspect of the invention, the skin condition is acne. In another preferred aspect of the invention, the skin condition is alopecia.

In a different aspect of the invention, the condition associated with diabetes is obesity, hypertension, hyperlipidemia, fatty liver disease, nephropathy, neuropathy, renal failure, retinopathy, diabetic ulcer, cataracts, insulin resistance syndrome, cachexia, a diabetic foot ulcer or a diabetic leg ulcer.

In yet another aspect of the invention, the condition associated with a cardiovascular dysfunction is coronary heart disease, cerebrovascular disease, hypertension, peripheral artery disease, occlusive arterial disease, angina, rheumatic heart disease, congenital heart disease, heart failure, cardiac insufficiency, palpitations, supraventricular tachycardia, fibrillation, faintness, dizziness, fatigue, migraine, high levels of total blood cholesterol and/or LDL cholesterol, low level of HDL cholesterol, high level of lipoprotein, infections of the heart such as carditis and endocarditis, diabetic ulcer, thrombophlebitis, Raynauds disease, claudication, gangrene, atherosclerosis or peripheral artery disease.

In one embodiment the metal poisoning is chronic. In a different embodiment, the metal poisoning is acute. Preferably, the metal is a heavy metal selected from the group consisting of calcium, aluminum, beryllium, cadmium, copper, iron, lead, uranium, plutonium, arsenic, molybdenum and mercury.

The composition to be administered in the methods of the invention may further comprise vitamins, salts, acids, vitamers, amino acids, or mixtures thereof, di-methyl amino ethanol and an antibiotic. In a preferred aspect of the invention, the antibiotic is erythromycin or gentamicin. In another preferred aspect of the invention, the composition to be administered further comprises lipoic acid and salts or mixtures thereof in an amount of about 250 mg. In yet another preferred aspect of the invention, the composition to be administered further comprises folic acid in an amount of about 400 mg. The composition may be administered by infusion over a period of about 1 minute to about 1 hour. The infusion may be repeated as necessary over a period of time selected from about 1 week to about 1 year. In another preferred aspect of the invention, the composition to be administered further comprises an anesthetic selected from the group consisting of lignocaine, bupivacaine, dibucaine, procaine, chloroprocaine, prilocalne, mepivacaine, etidocaine, tetracaine, lidocaine and xylocalne, and salts, derivatives and mixtures thereof. In yet another preferred aspect of the invention, the composition to be administered further comprises heparin.

In a preferred embodiment, the composition to be administered comprises sodium ascorbate, magnesium chloride $2H_2O$, 2 di-methyl amino ethanol HCl, thiamine, riboflavine, nicotinamide, pyridoxine, calcium pantothenate, cyanobalamin, and electroactivated water.

In yet another embodiment, the invention provides a method of reducing the amount of metal in a subject in need thereof comprising administering to the subject by injection a composition comprising a magnetic dipole stabilized solution. In a preferred aspect, the metal is a heavy metal having an oxidation state of +1, +2 or +3 selected from the group consisting of calcium, aluminum, beryllium, cadmium, copper iron, lead, uranium, plutonium, arsenic, molybdenum and mercury. Preferably, the metal is a transition or post-transition state metal. Even more preferably, the metal is a divalent cation. In another preferred aspect of the invention, the magnetic dipole stabilized solution is an electroactivated water having a negative electrical potential of about −990 to about −0.0001 mV, and comprising stabilized oxidative species selected from the group consisting of $H_2O$, $O_2$, $H_2O_2$, $Cl_2O$ and $H_3O$. Preferably, the solution comprises lipoic acid and salts or mixtures thereof in an amount of about 250 mg. In a preferred aspect of the invention, the composition is administered by infusion over a period of about 1 minute to about 1 hour. The infusion is repeated as necessary over a period of time selected from about 1 week to about 1 year. In a preferred aspect of the invention, the composition to be administered in the methods of the invention further comprises an anesthetic and one or more amino acids or salt thereof.

In another embodiment, the invention provides a method of increasing the excretion of metal or one or more toxins from a subject in need thereof, comprising administering to the subject by injection an effective amount of a magnetic dipole stabilized solution. Preferably, the magnetic dipole stabilized solution is an electroactivated water having a negative electrical potential of about −990 to about −0.0001 mV, and comprising stabilized oxidative species selected from the group consisting of $H_2O$, $O_2$, $H_2O_2$, $Cl_2O$ and $H_3O$.

In yet another embodiment, the invention provides a method of enhancing athletic, cognitive or alertness performance in a subject in need thereof comprising administering to the subject by injection an effective amount of magnetic dipole stabilized solution. Preferably, the magnetic dipole stabilized solution is an electroactivated water having a negative electrical potential of about −990 to about −0.0001 mV, and comprising stabilized oxidative species selected from the group consisting of $H_2O$, $O_2$, $H_2O_2$, $Cl_2O$ and $H_3O$. The composition may be administered by infusion over a period of about 1 minute to about 1 hour. The infusion may be repeated as necessary over a period of time selected from about 1 week to about 1 year within about 24 hours, within about one week or within about one month of the performance. In a preferred aspect of the invention, the magnetic dipole stabilized solution comprises sodium ascorbate, magnesium chloride $2H_2O$, 2 di-methyl amino ethanol HCl, thiamine, riboflavine, nicotinamide, pyridoxine, calcium pantothenate, cyanobalamin and electroactivated water. In another preferred aspect of the invention, the magnetic dipole stabilized solution comprises from about 100 mg to about 500 mg sodium ascorbate; from about 100 mg to about 500 mg magnesium chloride $2H_2O$; from about 100 mg to about 500 mg 2 di-methyl amino ethanol HCl; from about 1 mg to about 100 mg thiamine; from about 1 mg to about 100 mg riboflavine; from about 1 mg to about 300 mg nicotinamide; from about 1 mg to about 100 mg pyridoxine; from about 1 mg to about 100 mg calcium pantothenate; from about 100 µg to about 500 µg cyanobalamin; and electroactivated water.

In a further embodiment, the invention provides a method of providing nutritional support to a subject in need thereof comprising administering to the subject by injection an effective amount of magnetic dipole stabilized solution. Preferably, the magnetic dipole stabilized solution is an electroactivated water having a negative electrical potential of about −990 to about −0.0001 my, and comprising stabilized oxidative species selected from the group consisting of $H_2O$, $O_22$, $H_2O_2$, $Cl_2O$ and $H_3O$. The subject may be a healthy individual, or may be suffering from a malady selected from the group consisting of malnutrition, cachexia, diabetes, severe food allergies, short gut syndrome, cystic fibrosis, pancreatic disease, gastroenteritis, inflammatory bowel disease, intractable diarrhea, protein maldigestion, necrotizing enterocolitis, infectious diseases, hypermetabolism, trauma, eosinophilic gastroenteritis and gastroesophogeal reflux. In a preferred aspect of the invention, the magnetic dipole stabilized solution comprises one or more trace metals selected from the group consisting of Zn, Se, Cu, Mn and Fe. In a preferred embodiment, the subject receiving nutritional support has special dietary needs. Preferably, the dietary needs are associated with athletes, children, obese subjects, subjects undergoing chemotherapy for cancer, AIDS patients, malnourished subjects or subjects in a comatose state. In a preferred aspect of the invention, the magnetic dipole stabilized solution is an electroactivated water comprising from about 100 mg to about 500 mg sodium ascorbate; from about 100 mg to about 500 mg magnesium chloride $2H_2O$; from about 100 mg to about 500 mg 2 di-methyl amino ethanol HCl; from about 1 mg to about 100 mg thiamine; from about 1 mg to about 100 mg riboflavine; from about 1 mg to about 300 mg nicotinamide; from about 1 mg to about 100 mg pyridoxine; from about 1 mg to about 100 mg calcium pantothenate; from about 100 µg to about 500 µg cyanobalamin; from about 1 mg to about 20 mg Zn; from about 1 mg to about 100 mg Se; from about 1 mg to about 1000 mg Cu; from about 0.01 mg to about 10 mg Mn; and from about 1 mg to about 20 mg Fe. In another preferred aspect of the invention, the magnetic dipole stabilized solution comprises about 395 mg sodium ascorbate; about 255 mg magnesium chloride $2H_2O$; about 200 mg 2-di-methyl amino ethanol HCl; about 36 mg thiamine; about 7.3 mg riboflavine; about 100 mg nicotinamide; about 18.2 mg pyridoxine; about 18.2 mg calcium pantothenate; about 320 µg cyanobalamin; about 10 mg Zn; about 45 mg Se; about 400 mg Cu; about 0.3 mg Mn; about 8 mg Fe; and electroactivated water.

In a different embodiment, the invention provides a kit comprising a first vial containing a solution comprising vitamins, salts, acids, vitamers, or mixtures thereof, and a second vial containing a magnetic dipole stabilized solution comprising electroactivated water. Preferably, the kit comprises instructions for use. In a preferred aspect of the invention, the magnetic dipole stabilized solution has a positive electrical potential before mixing the contents of the vials. In an even more preferred aspect of the invention, the magnetic dipole stabilized solution has a negative electrical potential after combining the first and second vials. Preferably, the solution in the first vial comprises sodium ascorbate, magnesium chloride 2 $H_2O$, 2 di-methyl amino ethanol HCl, thiamine, riboflavine, nicotinamide, pyridoxine, calcium pantothenate, and cyanobalamin.

In another embodiment, the invention provides a kit comprising a first vial containing a magnetic dipole stabilized solution comprising electroactivated water and one or more selected from the group consisting of heparin, vitamins, salts, acids, lipoic acid, folic acid, antibiotic(s) and vitamers, and mixtures thereof; a second vial containing a magnetic dipole stabilized solution; and instructions for use. In a preferred aspect of the invention, the solution in the first vial comprises lipoic acid in an amount of between about 10 mg and 500 mg. Preferably, the amount of lipoic acid is between about 100 mg and 400 mg. Even more preferably, the amount of lipoic acid is about 250 mg. In another preferred aspect of the invention, the solution in the first vial comprises sodium ascorbate, magnesium chloride $2H_2O$, 2 di-methyl amino ethanol HCl, thiamine, riboflavine, nicotinamide, pyridoxine, calcium pantothenate, cyanobalamin, lipoic acid, folic acid, and antibiotic(s).

DETAILED DESCRIPTION

The present invention will now be described more fully hereinafter. However, many modifications and other embodiments of the present invention set forth herein will come to mind to one skilled in the art to which the invention pertains having the benefit of the teachings presented in the foregoing descriptions. Therefore, it is to be understood that the present invention is not to be limited to the specific embodiments disclosed and that modifications and other embodiments are intended to be included within the scope of the appended claims.

Methods of treating or ameliorating skin conditions, diabetic conditions, cardiovascular conditions, cancer and infections by administering a magnetic dipole stabilized solution (MDSS) are provided. Also provided are methods of chelating, reducing the amount of metal in a mammal, increasing the amount of excretion of metal from a mammal, enhancing performance and nutritional supplementation by administering a magnetic dipole stabilized solution (MOSS). The MDSS compositions herein possess properties that when administered to a subject in need thereof provide a therapeutic or cosmetic effect for the skin, enhance performance or nutritional support, treat or ameliorate diabetic conditions, cardiovascular conditions, cancer and infections, provide chelation, reduce the amount of metal in a subject and increase metal excretion from a subject. Among other properties, the compositions are capable of restoring cellular integrity and transmembrane potential, modulating cellular membrane permeability and enhancing the transfer of molecules and ions through the cell membranes. Data provided herein show that these properties have a beneficial result when administered to a subject for the conditions described herein. Surprisingly, the MDSS compositions comprising vitamins or other ingredients described herein are very effective even for conditions that have not responded to prior treatments. Because the MDSS compositions are safe and non-toxic, they can be administered prophylactically to prevent or reduce the likelihood of onset of the conditions or symptoms described herein. One example is administration of an MDSS composition subsequent to exposure to a substance that may lead to an increased risk of increased metal in the body.

The purpose of the chelating agent is, of course, to sequester metals, such as paramagnetic metals, heavy metals or radionuclides. Heavy metals include toxic metals and elements that exhibit metallic properties, which would mainly include the transition metals, some metalloids, lanthanides, and actinides. Suitable metals include calcium, aluminum, beryllium, cadmium, copper iron, lead, uranium, plutonium, arsenic and mercury. Other suitable paramagnetic metals include a lanthanide element of atomic numbers 58-70 or a transition metal of atomic numbers 21-29, 42 or 44, such as scandium, titanium, vanadium, chromium, manganese, iron, cobalt, nickel, copper, molybdenum, ruthenium, cerium, praseodymium, neodymium, promethium, samarium, europium, gadolinium, terbium, dysprosium, holmium, erbium, thulium, and ytterbium, most preferably Gd(III), Mn(II), iron, europium and/or dysprosium. Suitable radionuclides include the radioactive forms of, for example, Sm, Ho, Y, Pm, Gd, La, Lu, Yb, Sc, Pr, Tc, Re, Ru, Rh, Pd, Pt, Cu, Au, Ga, In, Sn, and Pb.

As used herein, the term "metal poisoning" refers to an excessive build-up of a particular metal in the mammal. The symptoms of metal poisoning are well known and differ depending on the particular metal and the mammal. A mammal can be asymptomatic but nevertheless be suffering from metal poisoning.

As used herein the term "mammal" refers to humans as well as all other mammalian animals. As used herein, the term "mammal" includes a "subject" or "patient" and refers to a warm blooded animal. It is understood that guinea pigs, dogs, cats, rats, mice, horses, goats, cattle, sheep, zoo animals, livestock, primates, and humans are all examples of animals within the scope of the meaning of the term. As used herein "a mammal in need thereof" may be a subject whom could have been but is not required to have been diagnosed as suffering from the condition intended to be treated. In one aspect, the present method is directed to conditions that are noticeable to the subject and the subject wishes to treat or ameliorate the condition without a formal diagnosis. For instance, a subject wishing to ameliorate alopecia is a subject who has hair loss or wishes to stave off subsequent hair loss. In another example, a subject with acne does not necessarily need to be diagnosed to know that he or she has acne. Alternatively, a subject could be diagnosed with a skin condition and seek treatment or amelioration by a method disclosed herein. Clearly, one who suffers from these conditions has an acute awareness of the problem with or without a formal diagnosis by medical personnel. Alternatively, one may be aware of symptoms associated with metal poisoning without knowing that metal poisoning may be causing the symptoms. One may wish to have chelation treatment to improve or ameliorate the symptoms. In other words, a mammal, if human, in need of being treated can appreciate the purpose for which he or she is being treated, whether it is to treat a symptom of a known or unknown cause or the underlying cause with or without formal diagnosis. Alternatively, a mammal in need thereof is one who has been diagnosed as having a condition and is in need of specific treatment.

As used herein the terms "treating" and "ameliorating" are intended to refer to all processes wherein there may be a slowing, interrupting, arresting, or stopping of the progression of the condition or symptoms and does not necessarily indicate a total elimination of the underlying condition. The terms also encompass the administration of a MDSS composition wherein the mammal has a condition or symptom or a predisposition towards a condition or symptom, where the purpose is to cure, heal, alleviate, relieve, alter, improve or affect the condition or symptom or the predisposition to the same. Also contemplated is preventing the condition or symptom or the predisposition to the same by prophylactically administering a MDSS composition as described herein.

As used herein, the term "skin condition" means a disorder, disease or symptom related to the skin. The term "skin" is meant to describe the outer covering of a mammalian form including, without limitation, the epidermis, dermis, and subcutaneous tissues. The skin can include other components such as hair follicles and sweat glands. A number of skin conditions can be treated according to the methods of the present invention and include skin disorders of the hair follicles and sebaceous glands. These and other conditions include, but are not limited to, intrinsic skin aging, wrinkles, acne, photodamage, rosacea, scars, hypertrophic scars, keliods, stretch marks or Striae distensae, psoriasis, nutrient status, anti-oxidant status, energy status, oxygen status, eicosanoid staus, leukotriene status, pruritus, ehlers-danlos syndrome, scleroderm a, post inflammatory hyperpigmentation, melasma, alopecia, poikiloderma of civatte, viteligo, skin cancers, skin dyschromas, or blotchy pigmentation. Preferably, skin conditions such as acne, alopecia and burns among others, can be treated according to the present invention. The skin consists in the widest organ existing in the human body. Among the functionalized structures present therein, the vascular system, lymphatic system, glands and nerves, are detached. Interaction of all its structures in an orderly manner, confers to the skin a fundamental role on existence and survival of the livings, constituting an efficient interface between external ambient and internal organs, which main function is to protect from water loss, contingent intruders, strange material, pathogenic organisms and microorganisms. Further to these functions, skin is able to eliminate a series of catabolites originating from internal biochemical processes and to maintain the ideal temperature constant for the adequate functioning of living organisms.

Skin is structurally composed of two tissue layers. The epidermis is the most external layer. It is constituted of a series of epithelium stratified cell layers, which quantity of keratin protein proportionally increases on most external layers. This arrangement makes the most external layers more compact, offering greater protection in relation to excessive water loss, action of strange substances and organisms, besides offering greater resistance to abrasion and injuries. This layer does not contain any blood vessel and is sustained by fluids of the layer immediately beneath the dermis, this one presenting irregular connection arrangements, presenting more complex tissues and containing blood vessels between a series of specialized structures.

Skin integrity can eventually be ruptured, causing a series of problems with reference to maintenance of the internal functions of the organism. This rupture can occur due to perforations, accidental or programmed cuts (surgeries), burns, injuries resulting from degenerating processes, having diseases, congenital anomalies or alterations of biochemical processes as a cause, resulting in ulceration, among others.

Under normal conditions, the body has mechanisms to repair and eventually recover, partial or totally, several skin ruptures, in order to restore its integrity and functionality. This repair process is directly related with rupture extension, tissues affected, injury and patient physical condition. Contamination of exposed tissue by strange substances and live organisms will be another factor that will influence on the mechanism and the velocity of the repair process. Skin healing process involves particular groups of cells and proteins in a complex biochemical mechanism. This renovation process is generally divided in three temporary phases known as inflammation, proliferation and remodeling.

At the initial stage of inflammation, the platelets present out of the circulatory system become more active, producing aggregation. Thus, they signalize the beginning of the repair process, forming a set of temporary cells to avoid hemorrhage and prevent bacterial invasion. Blood vessels under growth, infiltrates in the affected site, discharging various mediator molecules, including other platelets resulting from growth factors, Willibrand factor, thrombospondine, fibronectine, fibrinogen, 5-hydroxytriptophan, thromboxane-A2 and adenosine diphosphate (Kirsner e Eaglstein, J. Dermatol. 151:629-640, 1993). The set of cells that characterizes the clotting are bonded and provides a matrix of monocytes, fibroblasts and keratinocytes. Chemostatic molecules attract the monocytes that are transformed into macrophages and secreting additional growth factors (Nathan e Sporn. J. Cell Biol. 113:981-986, 1991). Neutrophyls can assist these processes secreting degrading enzymes, the elastases and collagenases, increasing the passage through the basis of cellular membrane. The most important role of the neutrophyls seems to be cleaning the affected tissue or defend the area from contingent intruders, accelerating the process as a whole, removing the dead cells and platelets. Infiltration of neutrophyls ceases within 48 hours approximately, provided that no bacterial contamination occurs. The neutrophyls excess is phagocyted by macrophages resulting from monocytes of the circulatory system. It is believed that the macrophages are essential for an efficient recovery process, also being responsible for the phagocytes process of pathogenic organisms and for the cleaning of other materials strange to the body. Moreover, they deliver innumerous factors involved in subsequent events in tissue recovery process.

The second recovery stage, the proliferation, generally begins 48 hours after occurring tissue injury. Fibroblasts begin to proliferate and migrate to the interior of affected space, starting from the already bond tissues and reaching the end of injury. Fibroblasts yield collagen and glycosaminoglycans, stimulating a proliferation of endothelial cells. Endothelial cells will promote the growth of a new net of blood vessels. Collagenases and plasminogen activators are secreted from keratinocytes. If the recovery process is not disturbed, an adequate supply of nutrients with oxygen, the keratinocytes can migrate to the affected tissue. It is believed that keratinocytes only migrate on live tissues and, as a consequence, keratinocytes migrate through areas beneath dead tissues and in interface between the affected area and that already recovered. Angiogenesis, formation of new blood vessels in response to chemotactic signals (Folkman and Klagsbrun, Science 235:442-447, 1987), and fibroplasias, accumulation of fibroblasts and formation of tissues granulation, also occur during the proliferating phase.

The third and last recovery stage, the remodeling, starts when the epithelium is already recovered. In this phase, which can be extended for many years, the affected tissue obtains its normal strength, slowly undergoing structural readjustments, always on account of depth, as well as the extension of the affected area. Remodeling of tissues is followed by the secretion of cellular matrix components, including fibronectine, collagen and proteoglycan, which serve as a support for the cellular migration and for the tissue. The type III collagen, synthesized at the initial stages of the recovery process, is substituted by type I collagen, the most permanent form, by a response proteolitic process. The affected surface is subsequently coated with an enlargement process, making the surface smoother. These epithelial cells are spread at layers underneath the unstructured area, in order that the affected layers and those above it are slowly substituted or recovered.

This complex process of natural regeneration takes considerable time and can be affected by pathological conditions as infections, maceration, dry skin and overall patient health. This can lead to chronic ulcer formation, making this process still slower. Other severe conditions can be established in tissues regeneration course. Ischemia, for example, refers to a pathological condition resulting from a located dysfunction of the vascular system, resulting in inadequate blood supply with subsequent damage to the affected cellular tissue.

The term "acne" is meant to include any skin condition where a skin pore becomes blocked and/or thereby becomes inflamed. The term acne includes without limitation superficial acne, including comedones, inflamed papules, superficial cysts, and pustules; and deep acne, including deep inflamed modules and pus-filled cysts. Specific acne conditions can include, but are not limited to, acne vulgaris, acne comedo, papular acne, premenstrual acne, preadolescent acne, acne venenata, acne cosmetica, pomade acne, acne detergicans, acne excoriee, gram negative acne, acne rosacea, pseudofolliculitis barbae, folliculitis, perioral dermatitis, and hiddradenitis suppurativa. Acne is a common inflammatory pilosebaceous disease characterized by comedones, papules, pustules, inflamed nodules, superficial pus-filled cysts, and (in extreme cases) canalizing and deep, inflamed, sometimes purulent sacs. Acne involves an interaction between hormones, keratinization, sebum, and bacteria that somehow determines the course and severity of acne. It often begins at puberty, when the increase in androgens causes an increase in the size and activity of the pilosebaceous glands. The earliest microscopic change is thought to be intrafollicular hyperkeratosis, which leads to blockage of the pilosebaceous follicle with consequent formation of the comedo, composed of sebum, keratin, and microorganisms, particularly *Propionibacterium acnes*. Lipases from *P. acnes* break down triglycerides in the sebum to form free fatty acids (FFA), which irritate the follicular wall. Retention of sebaceous secretions and dilation of the follicle may lead to cyst formation.

Skin conditions also include, but are not limited to, dermatological conditions linked to disorders of keratinization involving differentiation and proliferation, in particular, acne vulgaris, comedonic or polymorphic acne, nodulocystic acne, acne conglobata, senile acne and secondary *acnes* such as solar, drug or occupational acne; for other types of keratinization disorders especially ichthyoses, ichthyosiform conditions, Darier's disease, palmoplantar keratoderma, leukoplakia and luecoplakiform conditions or lichen and lichen planus; dermatological disorders having an inflammatory or immunoallergic component, in particular, all forms of psoriases, either cutaneous, mucosal or ungual, and psoriatic rheumatism, and cutaneous atopy such as eczema or respiratory atopy, dry skin, inflammation of the skin, solar erythema, skin allergies or other skin disorders of the epidermis and dermis.

Psoriasis is a skin condition characterized by hyperplasia of keratinocytes resulting in thickening of the epidermis and the presence of red scaly plaques. The lesions in this chronic disease typically are subject to remissions and exacerbations. There are several patterns, of which plaque psoriasis is the most common. Guttate psoriasis, with raindrop shaped lesions scattered on the trunk and limbs, is the most frequent form in children, while pustular psoriasis is usually localized to the palms and soles. The classical inflammatory lesions vary from discrete erythematous papules and plaques covered with silvery scales, to scaly itching patches that bleed when the scales are removed. Psoriasis is a condition in which cell proliferation is increased up to 10 times the normal rate for an individual. The skin is the largest portion of the human body which is comprised of cells within three skin layers. Each of the skin layers is in a constant state of growth with the outer layer being formed of predominantly dead tissue which is naturally being discarded at a normal rate. Replacement of cells from underlying layers is accomplished by cell division and maturation where cells move upwardly and outwardly at a rate which varies dependent upon the age, sex, and/or health of an individual. Psoriasis causes an increased turnover of cells, which in turn increases the rate of cell growth and cell death. This increased rate of cell growth and cell death may result in injuries and/or disorders which accompany the increased synthesis of all tissue components and further elevate the strain placed upon skin or other tissue and the bio-synthetic capabilities of the cells within the affected area.

The terms eczema and dermatitis are generally used names for severe inflammation of the skin, usually with redness, swelling, oozing, rusting or scaling of lesions which are usually itchy. Eczema may take the form of contact dermatitis (due to skin contact with the cause) or atopic dermatitis in individuals who are "atopic" or allergic by nature. If the scalp is involved the disorder is known as seborrheic dermatitis. Dermatitis can be caused by chemicals, plants, shoes, clothing, metal compounds and even medicines used to treat dermatitis. In atopic dermatitis environmental temperature, humidity changes, bacterial skin infections, airborne allergens and garments, e.g., wool, may all bring about dermatitis.

Alopecia is a skin condition that results in the loss of hair on the scalp and elsewhere. It usually starts with one or more small, round, smooth patches and occurs in males and females of all ages. Loss of hair in one or several small spots is common, but it is possible to lose all scalp hair (alopecia totalis), or every hair on the body (alopecia universalis), which is rare.

The skin condition, rosacea is of an unknown origin. It usually affects the middle third of the face causing skin redness, prominent vascularization, papules, pustules and swelling, as well as a predisposition to flushing and blushing. However, rosacea can also occur on other parts of the body including the chest, neck, back, or scalp. The blood vessels near the skin dilate and become more visible there through, resulting in telangiectasia. The resulting papules and pustules resemble teenage acne, and are frequently mistaken for the same. Unlike acne, rosacea does not have blackheads or whiteheads. Rosacea, however, can occur in all age groups and in both sexes, where it tends to be more frequent in women but more severe in men. The flushing and blushing regions of the face are affected by rosacea. Emotional factors such as anxiety, embarrassment, or stress may evoke or aggravate rosacea. In addition, a flare-up may be caused by environmental or climate variances, and UV exposure is known to aggravate rosacea. Furthermore, diet is also known to aggravate rosacea. Spicy foods, alcoholic beverages, hot beverages, and smoking are known to cause flare-ups. Rosacea is not only an aesthetic complication. Rosacea is a chronic disease that has rarely been documented to reverse its progression. If untreated, the condition worsens and spreads. Untreated rosacea may cause a disfiguring nose condition called rhinophyma, which is characterized by a bulbous, red nose and inflamed cheeks. Severe rhinophyma may require surgery, an invasive procedure that may be avoided by timely treatment. Another problem of advanced rosacea is ocular. Persons afflicted with rosacea may experience conjunctivitis, a burning and grittiness of the eyes. If untreated, it may lead to serious complications such as rosacea keratitis, which damages the cornea and may impair vision.

Burns involve a type of skin integrity rupture. Burns represent one of the most painful processes that can be established in this tissue, needing the establishment of a coordinated therapy to help its recovery and pain treatment. Burns can be caused by several factors, among which, exposure to high or low temperatures, exposure to chemical compounds, by electricity, by exposure to radiation and mechanical friction. Burn severity and its risk are evaluated according to the amount of affected tissue and depth reached. The amount of affected tissue is represented by the percentage of burned corporeal surface (BCS). In this type of evaluation, burns can be divided into small, moderate, large or massive burns, where regions inferior to 15% of BCS, from 15% up to 49% of BCS, from 50% up to 69% of BCS and over 70% of BCS, respectively. The extension of the affected area is determined through Lund-Browder scheme, which takes into consideration the burn proportion, in accordance with the age of the burned patient. Another rule that is most used for determining the extension of the affected area is that known as Wallace Rule or Rule of Nines, a technique less efficient than the foregoing, however, easy to memorize, being very much employed in emergency cases. This rule applies a value equaling nine or nine multiple to the affected parts, being 9% for each superior member, 9% for the head, 18% for each inferior member, 18% for each torso face and 1% for the genitalia.

The classification as first, second and third degree corresponds to burn depth. The first-degree injury corresponds to the burn that affects the skin most external layer (epidermis), not producing hemodynamic alterations, however the affected region is found hyperemic in absence of blisters or phlyctenae. This type of injury can be observed in erythemae resulting from sunrays or heated water. The second-degree injury affects either the epidermis as part of the dermis and is mainly characterized by the formation of blisters or phlyctenae, as those resulting from scalding or thermal injury resulting from overheated liquid. The third-degree injury endangers the totality of skin layers (epidermis and dermis) and, in many cases, can affect other tissues, as the subcutaneous cellular tissue, muscular tissue and bone tissue. Third-degree burns are considered as the most severe of all thermal injuries, producing deforming injuries. For being deeper, it eliminates the nerve endings responsible for shooting the painful message. These types of burns need transplanting for recomposing destroyed tissues, since the structures and organelles necessary for the natural recovery process, were eliminated. Since burns are wounds that involve the skin, they develop afore mentioned complex process of regeneration and recomposition of injured tissue. The speed or grade of re-epithelization of the affected region is small the greater the area involved is, considerably increasing the recovery time, when the injuries start to cover a body surface over 10% or 15%.

Immediately after the burn trauma, an inflammatory process develops wherein various agents are delivered, occurring deposition of fibrins and platelets activated on the wound surface. A matrix rich in organic material is yielded, able to enclosure bacteria and other strange substances, which frequently aggravates the case, due to sepsis that can follow trauma. During this inflammatory process a great quantity of exudates crop out of the burned region, leading the patient to an intense loss of liquids, which, depending on the burn extension and depth, can cause a severe dehydration case. The inflammatory process extends to adjacent tissues, factor that endangers the functions of these tissues initially intact.

Extensive and deep burns cause alterations that are extended far beyond the affected local, such as anatomic, metabolic, physiological, endocrinology and immune alterations, requiring special care. Significant fluid losses, delivery of inflammatory multi-mediators and contamination by bacteria, occur. When disseminated in central organs through circulation, bacteria and inflammatory mediators can cause cardiac endangerment, failure of gastrointestinal mucous integrity and in extreme cases, multi-organic failure.

Hemodynamic alterations that occur after severe thermal injuries include decrease of cardiac output and reduced volume of circulating plasma, contributing all to a hypovolemic shock. Inflammatory mediators (including cytokines, prostaglandin, nitric oxide and superoxide ions) have been implicated in causing further damage to tissues. It is believed that despite local benefit, such mediators induce undesirable effects when reaching significantly high levels. As an example, a greater damage to tissues can be caused by delivery of proteolitic enzymes and superoxide ions of macrophages and activated leucocytes.

Thus, burns are skin conditions that develop unbalance in a series of natural organic mechanisms, not limited to endangered tissues only, but involve numerous organs that can be affected. Additionally, large thermal injuries induce to a sharp increase in basal metabolic rate. Large nitrogen corporeal losses, observed in burned patients, mainly occur due to protein exudation through burned skin and also by the fact that, under such catabolic stress situation, corporeal proteins can become the metabolic substrate used for production of 15 to 20% of total energy required by the organism. Further to these abnormalities, hormonal levels change with an increase in cathecolamines, cortisol and glucagons, in the presence of normal or slightly increased levels of insulin. These hormonal alterations promote increase of proteolysis and lipolysis. Thus, the entire complex process is characterized by imbalance. The quick recovery of the skin of a burned mammal is of utmost importance for recovery of his normal organic functions.

Other skin conditions can include dry/chapped skin. Thus, the methods disclosed herein are useful for treating or ameliorating the skin against the effects of environmental conditions.

As used herein, a "condition associated with diabetes" includes obesity, hypertension, hyperlipidemia, fatty liver disease, nephropathy, neuropathy, renal failure, retinopathy, diabetic ulcer, cataracts, insulin resistance syndromes and cachexia. Diabetic diseases and conditions that are especially suited for treating or ameliorating with a MDSS composition as described herein are ulcers.

As used herein, "cardiovascular dysfunction" includes conditions and diseases such as coronary heart disease, cerebrovascular disease, hypertension, peripheral artery disease, occlusive arterial disease, angina, rheumatic heart disease, congenital heart disease, heart failure, cardiac insufficiency, palpitations, supraventricular tachycardia, fibrillation, faintness, dizziness, fatigue, migraine, high levels of total blood cholesterol and/or LDL cholesterol, low level of HDL cholesterol, high level of lipoprotein, infections of the heart such as carditis and endocarditis, diabetic ulcer, thrombophlebitis, Raynauds disease, claudication and gangrene. Diseases and conditions that are especially suited for treating or ameliorating with a MDSS composition as described herein are peripheral artery disease and atherosclerosis.

As used herein, the term "cancer" refers to a physiological condition in mammals that is typically characterized by unregulated cell growth/proliferation. Examples of cancer include but are not limited to, carcinoma, lymphoma, blastoma, sarcoma, and leukemia. More particular examples of such cancers include adrenocortical cancer; bladder cancer; bone cancer; brain cancer; breast cancer; cancer of the peritoneum; cervical cancer; colon cancer; colorectal cancer; endometrial or uterine carcinoma; esophogeal cancer; eye cancer; gallbladder cancer; gastrointestinal cancer; glioblastoma; various types of head and neck cancer; hepatic carcinoma; hepatocellular cancer; kidney cancer; laryngeal cancer; liver cancer; lung cancer, such as, for example, adenocarcinoma of the lung, small-cell lung cancer, squamous carcinoma of the lung, non-small cell lung cancer; melanoma and nonmelanoma skin cancer; myeloproliferative disorders, such as, for example, polycythemia vera, essential thrombocythemia, chronic idiopathic myelofibrosis, myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML, or juvenile myelomonocytic leukemia; ovarian cancer; pancreatic cancer; prostate cancer, including benign prostatic hyperplasia; rectal cancer; salivary gland carcinoma; squamous cell cancer; testicular cancer; thyroid cancer; and vulval cancer. Also contemplated is the use of a MDSS composition as an adjuvant to a primary therapy against one of the above-listed cancers. A cancer can be treated or ameliorated by treating or ameliorating a symptom of the cancer or secondary conditions of the cancer.

As used herein, the term "anti-infective" includes antiviral or antibiotic or any biostatic activity, i.e., where the proliferation of the target species is reduced or eliminated, and true biocidal activity where the target species are killed. Furthermore, the terms "microbe" or "antimicrobial" should be interpreted to specifically encompass bacteria and fungi as well as other single-celled organisms such as mold, mildew and algae. In this embodiment, it is preferred that the composition further comprise an antibiotic. The antibiotic can be an antibiotic effective against bacteria, including gram-negative and gram-positive organisms. Antibiotics include tetracycline, oxytetracycline, metacycline, doxycycline, minocycline, erythromycin, lincomycin, penicillin G, clindamycin, kanamycin, chloramphenicol, fradiomycin, streptomycin, norfloxacin, ciprofloxacin, ofloxacin, grepafloxacin, levofloxacin, sparfloxacin, ampicillin, carbenicillin, methicillin, cephalosporins, vancomycin, bacitracin, gentamycin, fusidic acid, ciprofloxin and other quinolones, erythromycin, gentamicin, sulfonamides, trimethoprim, dapsone, isoniazid, teicoplanin, avoparcin, synercid, virginiamycin, piperacillin, ticarcillin, cefepime, cefpirome, rifampicin, pyrazinamide, enrofloxacin, amikacin, netilmycin, imipenem, meropenem, inezolidcefuroxime, ceftriaxone, cefadroxil, cefazoline, ceftazidime, cefotaxime, roxithromycin, cefaclor, cefalexin, cefoxitin, amoxicillin, co-amoxiclav, mupirocin, cloxacillin, co-trimoxazole, pharmaceutically acceptable salts thereof, derivatives thereof, and combinations thereof. Especially preferred agents are erythromycin and gentamicin. The MDSS composition could alternatively or in addition to include one or more antiviral, antiseptic or antimicrobial agents.

As used herein, the term "metal poisoning" refers to an excessive build-up of a particular metal in a subject. The symptoms of metal poisoning are well known and differ depending on the particular metal and the subject. A subject can be asymptomatic but nevertheless be suffering from metal poisoning.

"Athletic performance" refers to any professional or recreational activity wherein the performer, for example an athlete, exerts a physical act, such as running, swimming, golf, bowling, archery, football, baseball, basketball, soccer, hiking, cycling, dancing and the like. "Cognitive performance" refers to any activity wherein the performer exerts a mental act and can include test-taking, focusing, concentrating, memorizing, studying and the like. A general state of "alertness" refers to the ability to focus or concentrate on a given task or performance. Alertness then can be viewed as an ability to stave off fatigue, mental tiredness or decreasing cognitive performance, such as when driving, boating, operating equipment, piloting, speech making, monitoring, police or security work, attending seminars and classes, working and the like. The magnetic dipole stabilized solution compositions described herein can be administered preferably before, but also during, long-lasting sports activities, any time an energetic boost is desired or when maintenance of energy levels is desired.

As used herein, the term "nutrition support" is intended to mean a composition that provides beneficial components that can include nutrients. The beneficial components are intended to work in conjunction with a separate primary nutrient source to meet the dietary needs of a mammal.

As used herein, the term "special dietary needs" refers to any mammal that has a restricted diet. The diet may be restricted because of allergy, but also because an unrestricted diet would likely cause the mammal to develop a food-borne condition. For example, the etiology of a number of gastrointestinal conditions is caused by the reaction towards certain foods in certain mammals. Subjects who are nauseous are also likely to have special diets in order to maintain a healthy nutrition. An example of this is cancer chemotherapy patients or AIDS patients. These individuals have difficulty maintaining an appetite or may be suffering from cachexia. Often children do not have appetites for various reasons and thus sometimes require a special diet to meet dietary needs. Individuals who are unconscious for long periods of time, for instance comatose patients will require special feeding solutions to maintain nutrition. The magnetic dipole stabilized solutions described herein can be useful adjuvants for helping to maintain dietary needs in situations such as these.

As used herein the term "enhancing performance" is intended to mean any improvement in performance. Performance can be assessed in any manner. Certain enhancements are readily measured. For example, in a timed-event, an improved time can assess an enhanced performance. Certain performance enhancing properties can be judged subjectively by the athlete or performer or an observer. In these instances, an enhanced performance means that the performance was perceived subjectively to be improved, magnified, faster, better and the like. The compositions described herein are effective for enhancing performance without the side effects of conventional stimulating agents such as caffeine or other substances banned from athletic competition or substances that a mammal cannot tolerate ingesting because of nausea or other conditions. Performance can be an athletic performance, a cognitive performance or a general state of alertness.

Thus, in one embodiment, the invention is directed to a method of treating or ameliorating a skin condition, a condition associated with diabetes, a condition associated with a cardiovascular dysfunction, a cancer, an infection, or metal poisoning in a subject in need thereof, or reducing the amount of metal in a subject in need thereof, or increasing metal excretion from a subject in need thereof, or enhancing performance of a subject or providing nutrition support to a subject in need thereof, comprising administering to the subject by injection a magnetic dipole stabilized solution composition. In a preferred aspect of the invention, the magnetic dipole stabilized solution comprises sodium ascorbate, magnesium chloride $2H_2O$, 2-di-methyl amino ethanol HCl, thiamine, riboflavine, nicotinamide, pyridoxine, calcium pantothenate cyanobalamin, and electroactivated water. In a preferred aspect, the magnetic dipole stabilized solution comprises from about 100 mg to about 500 mg sodium ascorbate, from about 100 mg to about 500 mg magnesium chloride $2H_2O$, from about 100 mg to about 500 mg 2 di-methyl amino ethanol HCl, from about 1 mg to about 100 mg thiamine, from about 1 mg to about 100 mg riboflavine, from about 1 mg to about 300 mg nicotinamide, from about 1 mg to about 100 mg pyridoxine, from about 1 mg to about 100 mg calcium pantothenate, from about 100 µg to about 500 µg cyanobalamin, and electroactivated water. In another preferred aspect of the invention, the magnetic dipole stabilized solution further comprises folic acid and/or an antibiotic. In one aspect of the invention, the treatment or amelioration of a skin condition comprises contacting the skin area to be treated or ameliorated with the solution. In a different aspect of the invention, the magnetic dipole stabilized solution used for the treatment or prevention of cancer further comprises vitamin K2.

In another embodiment, the invention is directed to a method of treating or ameliorating a skin condition that is an infection, comprising administering to a subject by injection a magnetic dipole stabilized solution, wherein the infection is treated or ameliorated. In this regard the method can be said to be an anti-infective treatment. In a preferred embodiment, the magnetic dipole stabilized solution comprises electroactivated water. The magnetic dipole stabilized solution for injection preferably has a negative or neutral electric potential.

In another embodiment, the present disclosure is directed to a method of treating or ameliorating a skin condition, a condition associated with diabetes, a condition associated with a cardiovascular dysfunction, a cancer, an infection, or metal poisoning in a subject in need thereof, or reducing the amount of metal in a subject in need thereof, or increasing metal excretion from a subject in need thereof, or enhancing performance of a subject or providing nutrition support to a subject in need thereof, comprising administering to a subject in need thereof by injection a magnetic dipole stabilized solution composition comprising, sodium ascorbate, magnesium chloride $2H_2O$, 2 di-methyl amino ethanol HCl, thiamine, riboflavine, nicotinamide, pyridoxine, calcium pantothenate, cyanobalamin, lipoic acid and electroactivated water. The solution may further include folic acid and/or an antibiotic.

In another embodiment, the present invention is directed to a method of treating or ameliorating a skin condition, a condition associated with diabetes, a condition associated with a cardiovascular dysfunction, a cancer, an infection, or metal poisoning in a subject in need thereof, or reducing the amount of metal in a subject in need thereof, or increasing metal excretion from a subject in need thereof, or enhancing performance of a subject or providing nutrition support to a subject in need thereof, comprising administering to a subject in need thereof by injection a magnetic dipole stabilized solution composition comprising, sodium ascorbate, magnesium chloride $2H_2O$, 2 di-methyl amino ethanol HCl, thiamine, riboflavine, nicotinamide, pyridoxine, calcium pantothenate, cyanobalamin, lipoic acid, folic acid and electroactivated water. The solution may further include an antibiotic.

In another embodiment, the present invention is directed to a method of treating or ameliorating a skin condition, a condition associated with diabetes, a condition associated with a cardiovascular dysfunction, a cancer, an infection, or metal poisoning in a subject in need thereof, or reducing the amount of metal in a subject in need thereof, or increasing metal excretion from a subject in need thereof, or enhancing performance of a subject or providing nutrition support to a subject in need thereof, comprising administering to a subject in need thereof by injection a magnetic dipole stabilized solution composition comprising, sodium ascorbate, magnesium chloride $2H_2O$, 2 di-methyl amino ethanol HCl, thiamine, riboflavine, nicotinamide, pyridoxine, calcium pantothenate, cyanobalamin, lipoic acid, folic acid, one or more antibiotics and electroactivated water.

In another embodiment, the present subject matter is directed to a composition for treating or ameliorating diseases comprising sodium ascorbate, magnesium chloride $2H_2O$, 2 di-methyl amino ethanol HCl, thiamine, riboflavine, nicotinamide, pyridoxine, calcium pantothenate, cyanobalamin and electroactivated water. The composition may further include lipoic acid, folic acid and/or one or more antibiotics.

Preferably, sodium ascorbate is present in an amount equivalent to ascorbic acid from about 0.01 g to about 10 g per dose (preferably in a 10 ml dose). Preferably, the amount is from about 0.1 g to about 1.0 g per dose. More preferably, the amount is from about 0.24 g to about 0.9 g per dose.

Preferably, magnesium chloride is present in an amount from about 0.01 g to about 10 g per dose (preferably in a 10 ml dose). Preferably, the amount is from about 0.1 g to about 1.0 g per dose. More preferably, the amount is from about 0.5 g to about 0.8 g per dose.

Preferably, dimethyl amino ethanol HCl, is present in an amount from about 0.01 g to about 10 g per dose (preferably in a 10 ml dose). More preferably, the amount is from about 0.1 g to about 1.0 g per dose. Even more preferably, the amount is from about 0.2 g to about 0.87 g per dose.

Preferably, thiamine is present in an amount from about 0.01 g to about 10 g per dose (preferably in a 10 ml dose). More preferably, the amount is from about 0.1 g to about 1.0 g per dose. Even more preferably, the amount is from about 0.12 g to about 0.15 g per dose.

Preferably, riboflavin is present in an amount from about 0.001 g to about 1.0 g per dose (preferably in a 10 ml dose). More preferably, the amount is from about 0.01 g to about 1.0 g per dose. Even more preferably, the amount is from about 0.01 g to about 0.02 g per dose.

Preferably, nicotinamide is present in an amount from about 0.01 g to about 10 g per dose (preferably in a 10 ml dose). More preferably, the amount is from about 0.1 g to about 1.0 g per dose. Even more preferably, the amount is from about 0.10 g to about 0.15 g per dose.

Preferably, pyridoxine is present in an amount from about 0.01 g to about 10 g per dose (preferably in a 10 ml dose). More preferably, the amount is from about 0.1 g to about 1.0 g per dose. Even more preferably, the amount is from about 0.55 g to about 0.65 g per dose.

Preferably, calcium pantothenate is present in an amount from about 0.001 g to about 1.0 g per dose (preferably in a 10 ml dose). More preferably, the amount is from about 0.01 g to about 1.0 g per dose. Even more preferably, the amount is from about 0.03 g to about 0.04 g per dose.

Preferably, cyanobalamin is present in an amount from about 0.1 g to about 10 g per dose (preferably in a 10 ml dose). More preferably, the amount is from about 1 g to about 5 g per dose. Even more preferably, the amount is from about 1.8 g to about 2.25 g per dose.

Preferably, vitamin K2 is present in an amount from about 0.01 mg to 125 mg per dose (preferably in a 10 ml dose), including about 1 mg, about 5 mg, about 20 mg, about 50 mg, about 75 mg and about 100 mg per dose.

When lipoic acid, its salts or mixtures thereof are present, the amount of lipoic acid is preferably from about 10 mg to about 500 mg. Also preferred is an amount from about 100 mg to about 400 mg. More preferably, the amount is from about 250 mg to about 350 mg. Most preferably, the amount is about 250 mg. Solubility modifiers including, but not limited to, emulsifying agents such as phosphatidylcholine, can be used if needed to formulate the lipoic acid in a desired amount.

When folic acid, its salts or mixtures thereof is present, the amount of folic acid is preferably from about 0.001 g to about 10 g per dose (preferably in a 10 ml dose), including about 0.01 g, about 0.1 g, about 1 g and about 5 g per dose. Preferably, the amount is from about 0.1 g to about 1.0 g per dose. More preferably, the amount is from about 0.2 g to about 0.5 g per dose. Solubility modifiers can be used if needed to formulate the lipoic acid in a desired amount.

One or more of an antibiotic, antiviral, antimicrobial or antiseptic agent can be combined with MDSS to form a solution or the agent(s) can be combined with a MDSS to form a composition. The agents contemplated are those that are known in the art including, but not limited to, amoxicillin, levofloxacin, gatifloxacin, streptomycin, tetracycline, chloramphenicol, fluconazole, itraconazole and posaconazole. Effective amounts of these agents are also known. In particular, the MDSS compositions and solutions comprise erythromycin in about 500 mg per MDSS dose and/or about 30 mg of gentamicin per MDSS dose.

In a different embodiment, the present invention is directed to a method of reducing the amount of a metal(s) in a subject in need thereof, increasing the excretion of a metal(s) or treating or ameliorating metal poisoning. In one aspect, the metal is a heavy metal. In another aspect, the metal is selected from the group consisting of calcium, lead, uranium, plutonium, arsenic, molybdenum and mercury. In another aspect, the metal has an oxidation state of +1, +2 or +3. In another aspect, the metal is a transition or post-transition state metal. In another aspect, the metal is a divalent cation. Preferably, the metal is selected from the group consisting of $Fe^{+3}$, $HG^{+2}$, $Cu^{+2}$, $Ar^{+3}$, $Pb_{+2}$, $Co_{+2}$, $Cd_{+2}$ and $Mn_{+2}$. In one aspect, the metal poisoning is acute. In a different aspect, the metal poisoning is chronic. In a preferred embodiment, the MDSS solution for chelation comprises glycine. Glycine can complex with divalent cations and enhance the metal sequestering and/or reducing effect.

In another embodiment, the present invention is directed to a method of increasing the excretion of one or more toxins from a mammal, comprising administering to a subject by injection an effective amount of magnetic dipole stabilized solution, wherein said excretion of one or more toxins is increased. In this embodiment, the toxins are more soluble in the electroactivated water and are eliminated from the body by excretion.

In yet another embodiment, the present invention is directed to a method of providing nutrition support to a subject in need thereof, comprising administering to the subject an effective amount of magnetic dipole stabilized solution. The subject receiving nutritional support according to the invention may be a healthy subject, or a subject suffering from a malady selected from the group consisting of malnutrition, cachexia, diabetes, severe food allergies, short gut syndrome, cystic fibrosis, pancreatic disease, gastroenteritis, inflammatory bowel disease, intractable diarrhea, protein maldigestion, necrotizing enterocolitis, infectious diseases, hypermetabolism, trauma, eosinophilic gastroenteritis or gastroesophogeal reflux.

In another embodiment, the present invention is directed to a method wherein the magnetic dipole stabilized solution comprises one or more trace metals selected from the group consisting of Zn, Se, Cu, Mn and Fe. In a preferred embodiment, the magnetic dipole stabilized solution is an electroactivated water comprising from about 100 mg to about 500 mg sodium ascorbate, from about 100 mg to about 500 mg magnesium chloride $2H_2O$, from about 100 mg to about 500 mg 2 di-methyl amino ethanol HCl, from about 1 mg to about 100 mg thiamine, from about 1 mg to about 100 mg riboflavine, from about 1 mg to about 300 mg nicotinamide, from about 1 mg to about 100 mg pyridoxine, from about 1 mg to about 100 mg calcium pantothenate, from about 100 μg to about 500 μg cyanobalamin, from about 1 mg to about 20 mg Zn, from about 1 mg to about 100 mg Se, from about 1 mg to about 1000 mg Cu, Mn from about 0.01 mg to about 10 mg, from about 1 mg to about 20 mg Fe and electroactivated water. In a more preferred embodiment, the magnetic dipole stabilized solution comprises about 395 mg sodium ascorbate, about 255 tug magnesium chloride $2H_2O$, about 200 mg 2-di-methyl amino ethanol HCl, about 36 mg thiamine, about 7.3 mg riboflavine, about 100 mg nicotinamide, about 18.2 mg pyridoxine, about 18.2 mg calcium pantothenate, about 320 μg cyanobalamin, about 10 mg Zn, about 45 mg Se, about 400 mg Cu, about 0.3 mg Mn, about 8 mg Fe, and electroactivated water.

In one aspect of the invention, the subject receiving nutritional support has special dietary needs. The method comprises administering to a subject in need thereof by injection an effective amount of magnetic dipole stabilized solution as described herein. Preferably, the special dietary needs are associated with athletes, children, obese subjects, subjects undergoing chemotherapy for cancer, malnourished subjects or subjects in a comatose state. In a preferred embodiment, the method of the invention is for aiding in weight loss. Weight gain is caused by consuming more calories than the body requires for its basal metabolic functions and additional activities in which an individual is involved. The human body stores these excess calories as fatty deposits (lipids in adipose tissue) throughout the body, but is not able to readily access these fatty deposits to satisfy energy needs. To use these stored lipids as an energy source, the number of calories ingested must be less than the total energy expenditure of the body (basal metabolic rate plus activity level). Under hypocaloric conditions the body consumes fat as a source of fuel, but the switch to energy utilization of stored fat is not instantaneous. The body has feedback mechanisms that attempt to preserve existing lipid stores. Therefore, in the interim between the initial reduction in caloric intake and the conversion of lipids to energy, the body consumes lean body mass as a source of energy. Hepatic gluconeogenesis utilizes amino acids from muscle to generate glucose which the body uses as its preferred energy source. Hence, the body will consume some muscle tissue as its energy source during this period of conversion. Reduced caloric intake usually induces cravings for food that reduce adherence to weight loss regimens. These cravings are caused by both psychological and physiological mechanisms. For example, ingested carbohydrates are absorbed from the digestive tract into the bloodstream to increase blood glucose levels. In response to the increase in blood glucose, the pancreas releases insulin to aid in the transport of glucose into the cells of the body where glucose is employed as an energy source. However, if the amount of insulin released is greater than the amount of glucose present (which is often the case in overweight individuals), then the body reacts by signaling the brain to ingest more carbohydrates in order to balance the amount of insulin in the bloodstream. This insulin-induced craving for carbohydrates is very common during periods of caloric restriction. The MDSS solutions described herein can treat or ameliorate the symptoms associated with a reduced caloric intake.

In yet another embodiment, the present invention is directed to a method of treating or ameliorating symptoms related to menopause. Menopause is a period after the cessation of normal ovulation cycles, during which normal menstruation ceases. A decrease in estradiol ($E_2$) production accompanies menopause, as the ovaries cease manufacture of $E_2$. This decrease in $E_2$ production results in a shift in hormone balance in the body, which often gives rise to a variety of symptoms associated with menopause. Peri-menopause, which is also known as pre-menopause or the climacteric, is a period prior to menopause during which normal ovulation cycles gradually give way to cessation of menses. As the ovulatory cycles lengthen and become more irregular, the level of $E_2$ may initially increase, but will eventually drop with the onset of menopause. Menopausal symptoms often accompany the drop in $E_2$ levels. The symptoms of peri-menopause, menopause and post-menopause include physical symptoms such as hot flashes and sweating secondary to vasomotor instability. Additionally, psychological and emotional symptoms may accompany onset of climacteric, such as fatigue, irritability, insomnia, inability to concentrate, depression, memory loss, headache, anxiety and nervousness. Additional symptoms can include intermittent dizziness, paresthesias, palpitations and tachycardia as well as nausea, constipation, diarrhea, arthralgia, myalgia, cold hands and feet and weight gain. In addition, changes to the genitals, urinary incontinence, vaginal dryness, loss of pelvic muscle tone, increased risk of cardiovascular disease and osteoporosis increase with onset of menopause. Hot flashes are prevalent in, and bothersome to, many peri-menopausal, menopausal and postmenopausal women. For decades hormone replacement therapy with estrogens has been the standard treatment for hot flashes, but many women have abandoned hormone therapy (HT) due to concerns about potential adverse effects, particularly breast cancer. The MDSS compositions described herein are useful in treating or ameliorating one or more of the symptoms described above. In an embodiment, the method comprises administering to a female subject in need thereof by injection an effective amount of magnetic dipole stabilized solution as described herein.

In another embodiment, the present invention is directed to a kit comprising a first vial containing a solution comprising one or more selected from the group consisting of heparin, vitamins, salts, acids, lipoic acid, folic acid, antibiotic(s) and vitamers, and mixtures thereof; a second vial containing a magnetic dipole stabilized solution; and optionally instructions for use. Preferably, the first vial contains one or more selected from the group consisting of vitamins, salts, acids and vitamers and mixtures thereof. Preferably in one aspect of this embodiment, the magnetic dipole stabilized solution contained in the kit is electroactivated water. In another aspect, the first vial preferably comprises lipoic acid and the amount of lipoic acid is preferably from about 10 mg to about 500 mg. Preferably, the amount of lipoic acid is from about 100 mg to about 400 mg. More preferably, the amount of lipoic acid is from about 250 mg to about 350 mg. Most preferably, the amount of lipoic acid is about 250 mg. Solubility modifiers can be used if needed to formulate the ingredients, including the lipoic acid, in a desired amount.

In a preferred embodiment, the kit contains a first vial comprising sodium ascorbate, magnesium chloride $2H_2O$, 2 di-methyl amino ethanol HCl, thiamine, riboflavine, nicotinamide, pyridoxine, calcium pantothenate and cyanobalamin. Optionally, the first vial can contain folic acid, lipoic acid and/or an antibiotic, such as erythromycin or gentamicin.

In another embodiment, the present subject matter is directed to a kit comprising, a first vial containing a solution comprising, from about 100 mg to about 500 mg sodium ascorbate, from about 100 mg to about 500 mg magnesium chloride $2H_2O$, from about 100 mg to about 500 mg 2 di-methyl amino ethanol HCl, from about 1 mg to about 100 mg thiamine, from about 1 mg to about 100 mg riboflavine, from about 1 mg to about 300 mg nicotinamide, from about 1 mg to about 100 mg pyridoxine, from about 1 mg to about 100 mg calcium pantothenate, from about 100 μg to about 500 μg cyanobalamin, from about 1 mg to about 20 mg Zn, from about 1 mg to about 100 mg Se, from about 1 mg to about 1000 mg Cu, from about 0.01 mg to about 10 mg Mn and from about 1 mg to about 20 mg Fe, and a second vial containing a magnetic dipole stabilized solution; and optionally instructions for use. In a preferred embodiment, the magnetic dipole stabilized solution is electroactivated water. Preferably, the magnetic dipole stabilized solution comprises electroactivated water.

Electroactivated water can be prepared using methods, apparatus, and systems disclosed in, for example, Van Kalken et al., International Patent Application No. PCT/US2011/020691, Davis et al. U.S. Pat. No. 7,374,645, and/or Daly et al. U.S. Pat. No. 7,691,249, which are incorporated herein by reference. The ORP of the electroactivated water is that of the neutral anolyte, which has a positive ORP, preferably above +100 mV. Also preferred are values of above +200 mV, above +300 mV, +400 mV, above +500 mV, +600 mV, above +700 mV, +800 mV, above +900 mV and +1000 mV. The magnetic dipole stabilized solution for injection however preferably has a negative or neutral electric potential once additional components, e.g., vitamins are combined to the contents of vials in a kit are combined. In a preferred embodiment of this aspect, the negative potential is below about −990 mV. In a preferred embodiment, the potential is from about −990 mV to about −0.0001 mV. More preferably, the potential is from about −150 mV to about −5 mV. Also more preferred is a potential from about −120 mV to about −20 mV. Most preferably, the potential is about −70 mV.

In one embodiment, the MDSS composition comprises 2-(diethylamino)-N-(2,6-dimethylphenyl) acetamide or derivatives thereof. Not to be bound by theory, the MDSS can hydrolyze the active ingredient in situ thereby enhancing its effect on channel blocking, cyclooxigenase activity and enzyme induction. More particularly, when 2-(diethylamino)-N-(2,6-dimethylphenyl) acetamide is present in the MDSS solution, it can be hydrolysed in situ to form the analogues of formula (I):

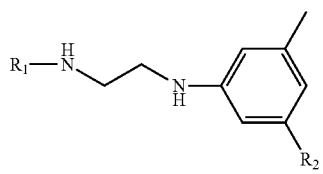

I wherein, $R_1$ is an alkyl, carboxamide or aminocarbamyl moiety; and $R_2$ is a methyl, ethyl, methoxy or carbonyl moiety. The pharmaceutical composition may include between 2.5% and 3.5% of the active ingredient and may have a pH of about 2.5 to about 3.5.

In an embodiment, a method is provided for activating a pharmaceutical composition in situ, the pharmaceutical composition including an active ingredient selected from the group consisting of 2-(diethylamino)-N-(2,6-dimethylphenyl) acetamide and its analogues, pharmaceutically acceptable salts, metabolites and esters thereof; and a carrier in the form of a magnetic dipole stabilized solution having antimicrobial properties; wherein a source of carbon dioxide is provided in the pharmaceutical composition prior to administration thereof. The source of carbon dioxide may be sodium bicarbonate. It is envisaged that the introduction of a source of carbon dioxide shall enhance the activity of the ionized portion of the active ingredient so as to thereby increase the efficacy of the pharmaceutical composition.

The magnetic dipole stabilized solution can further comprise other components. Specifically, the magnetic dipole stabilized solution, which preferably comprises electroactivated water, further comprises one or more independently selected from the group consisting of vitamins, salts, acids, amino acids or salts thereof, vitamers, di-methyl amino ethanol, anesthetic(s), stabilized oxidative species, heparin and lipoic acid, and mixtures thereof. Thus, in some embodiments, the pharmaceutical composition may further include nutrients suitable as cofactors for enzymes, vitamins suitable for rapid cellular energy production, pH modifiers and buffer components. The nutrients may be selected from the group consisting of amino acids, carbohydrates and lipids, and a combination thereof. In some embodiments, the combination of nutrients with MDSS can result in a synergistically enhanced effect of the active ingredient. More particularly, the nutrients are electro activated by the MDSS and improved delivery across the cell membrane thereof.

Carbohydrates, such as simple or complex sugars or cyclic oligosaccharides, can be a component of a MDSS composition. Preferably, the carbohydrate is fructose or a cyclodextrin, such a betacyclodextrin or hydroxypropyl cyclodextrin. When present, the cyclodextrin is in an amount of from about 0.001 to about 10 mg. Preferably, the amount is from about 0.05 to about 1.0 mg. Most preferably, the amount is from about 0.01 to about 0.5 mg.

Other compounds and molecules that can be a component of a MDSS solution are molecules, which also referred to as minerals. Those that are needed by the body in relatively large amounts are sodium, potassium, chlorine, calcium, phosphorus and magnesium. Those that are needed in smaller amounts are "trace" minerals and include selenium, iron, zinc, manganese, molybdenum, chromium, fluoride, iodine, copper and the like.

Another component of a MDSS composition can be one or more amino acids or salts or esters thereof. Preferably, the amino acid(s) is selected from the group consisting of glycine, alanine, arginine, glutamic acid and tyrosine and salts or esters thereof.

A preferred component is lipoic acid. Lipoic acid can be a racemic mixture or can be separated into its R and S enantiomers. The R enantiomer form of lipoic acid is preferred because it is the natural form. It has the structure:

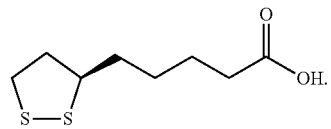 [SMILES: O=C(O)CCCC[C@@H]1CCSS1]

Buffer components selected from the group consisting of phosphoric acid and its salts or acetic acid and its salts, and pH modifiers selected from the group consisting of succinic acid, sulphuric acid, hydrochloric acid, sodium hydroxide, sodium bicarbonate and ethanolamine compounds, may also be included in the composition.

Oxidative species which can be in the composition are selected from the group consisting of $H_2O$, $O_2$, $H_2O_2$, $Cl_2O$, $H_3O$, $O_3$ and $ClO_3$.

An effective amount is the amount required to provide the subject with an improvement in a symptom or underlying condition. Many conditions can have subjective markers to gauge improvement, such as in the case of alopecia and acne. Therefore an effective amount is an amount that provides an improvement as gauged by the subject or by the provider. Some conditions have clinical markers. In these cases, an effective amount is an amount that provides an improvement by way of markers determined by clinical assessment. This, of course, is only one way of gauging an improvement in the symptom or condition to be treated. Finally, some conditions can have improvement based on subjective and/or clinical markers. The MDSS compositions will generally be used in an amount effective to achieve the intended result, for example in an amount effective to treat, prevent the particular condition in the first place or ameliorate the symptoms. MDSS compositions can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a MDSS composition to a patient suffering from a skin condition provides therapeutic benefit not only when the underlying skin condition is eradicated or ameliorated, but also when the patient reports a decrease in the severity or duration of the symptoms associated with the skin condition. Therapeutic benefit also includes halting or slowing the progression of the disease, regardless of whether improvement is realized.

A therapeutically effective amount of the compositions of the present invention will generally mean administration of from about 0.001 ml/kg to about 1.0 ml/kg (weight of active solution/body weight of mammal). Preferably the amount is from about 0.01 ml/kg to about 1.0 ml/kg. However, an effective amount may vary from mammal to mammal and can easily be adjusted by one of ordinary skill by varying the volume and frequency of administrations. The amount of composition administered will depend upon a variety of factors, including, for example, the particular indication being treated, the mode of administration, whether the desired benefit is prophylactic or therapeutic, the severity of the indication being treated and the age and weight of the patient, the bioavailability of the particular composition, and the like. Determination of an effective dosage is well within the capabilities of those skilled in the art coupled with the general and specific examples disclosed herein. When used prophylactically, the same principles and guidelines of dosing apply. The administration can occur in one infusion, but more preferably is delivered over one to five infusions per week, lasting for several weeks or months.

Practice of the method of the present invention comprises administering to a subject a therapeutically effective amount of a MDSS composition in any suitable systemic or local formulation, in an amount effective to deliver a dosage. In practicing the method of treatment or use of the present methods, a therapeutically effective amount of a MDSS composition is administered to a mammal either alone or in combination with other therapies. A preferred combination in all embodiments includes a method of administering a magnetic dipole stabilized solution combined with a separate vitamin regimen. As used herein, the term "regimen" means a deliberate administration or consumption of one or more vitamin(s) either as a single dose or as daily or weekly dosages. In these embodiments, the vitamins can be administered or consumed in any fashion to provide a mammal with the desired amount of vitamin(s). In these embodiments, the MDSS composition itself may or may not include vitamins. In other words, it is contemplated that the methods include administration of an MDSS composition in combination with vitamins, wherein the vitamins are administered or consumed in a separate composition either contemporaneous with the administration of an MDSS composition or at a different time. The period of time between the MDSS administration and the vitamin(s) administration or consumption can be a day, a week or more. The MDSS therapies described herein are preferably provided in administrations over weeks. Thus, any vitamin regimen within that time is contemplated in the methods described herein. More preferred time periods are MDSS administration within about one week of vitamin(s) administration or consumption. More preferably, an MDSS administration is within about one day of the vitamin(s) administration or consumption. Preferably, the vitamin regimen comprises a vitamin supplement or multivitamin consumed orally as a one-time dose or daily or weekly doses. Particularly preferred are vitamin regimens that provide a multivitamin or a composition comprising one or more of the vitamins disclosed herein in the disclosed amounts. More specifically, the vitamins are selected from families of vitamins selected from the group consisting of A (2000 to 25000 IU/dose), B1 (10 to 100 mg/dose), B2 (1 to 400 mg/dose), B3 (10 to 200 mg/dose), B5 (25 to 100 mg/dose), B6 (1 to 200 mg/dose), B12 (0.4 to 1500 µg/dose), C (10 to 2000 mg/dose), D (200 to 800 IU/dose), E (6 to 800 IU/dose) and K (70 to 500 µg/dose) and vitamers thereof. Also contemplated are combination therapies that include other supplements such as an antioxidant, beta-carotene, chromium picolinate, co-enzyme Q-10, conjugated linoleic acid, fish oil, iodine, L-arginine, Lecithin, L-lysine, Lutein, trace metals, soy isoflavones, glucosamine, chondroitin, melatonin, St. John's wort, pantothenic acid and S-adenosylmethionine. Again, just as described above for vitamin(s), these supplements are administered in combination with MDSS but not necessarily at the same time or in the same composition.

Routes of administration for a therapeutically effective amount of an MDSS composition include, but are not limited to, intravenous or parenteral administration, oral administration, topical administration, transmucosal administration and transdermal administration. For intravenous or parenteral administration, i.e., injection or infusion, the MDSS composition may also contain suitable pharmaceutical diluents and carriers, such as water, saline, dextrose solutions, fructose solutions, ethanol, or oils of animal, vegetative, or synthetic origin. It may also contain preservatives, and buffers as are known in the art. When a therapeutically effective amount is administered by intravenous, cutaneous or subcutaneous injection, the solution can also contain components to adjust pH, isotonicity, stability, and the like, all of which is within the skill in the art. A MDSS composition for intravenous, cutaneous, or subcutaneous injection should contain, in addition to peptide an isotonic vehicle such as Sodium Chloride Injection, Ringer's Injection, Dextrose Injection, Dextrose and Sodium Chloride Injection, Lactated Ringer's Injection Citrate Buffer pH 5.5, or other carriers, diluents and additives as known in the art. As described fully elsewhere herein, the pharmaceutical composition of the present invention may also contain stabilizers, preservatives, buffers, antioxidants, or other additive known to those of skill in the art. The pharmaceutical compositions are formulated for intravenous or parenteral administration. Typically, compositions for intravenous or parenteral administration comprise a suitable sterile solvent, which may be an isotonic aqueous buffer or pharmaceutically acceptable organic solvent. As described fully elsewhere herein, where necessary, the compositions can also include a solubilizing agent. Compositions for intravenous or parenteral administration can optionally include a local anesthetic to lessen pain at the site of the injection. Generally, the ingredients are supplied either separately or mixed together in unit dosage form in a hermetically sealed container such as an ampoule or sachette. The pharmaceutical compositions for administration by injection or infusion can be dispensed, for example, with an infusion bottle containing, for example, sterile pharmaceutical grade water or saline. Where the pharmaceutical compositions are administered by injection, an ampoule of sterile water for injection, saline, or other solvent such as a pharmaceutically acceptable organic solvent can be provided so that the ingredients can be mixed prior to administration.

The duration of intravenous therapy using the pharmaceutical composition of the present invention will vary, depending on the condition being treated or ameliorated and the condition and potential idiosyncratic response of each individual mammal. The duration of each infusion is from about 1 minute to about 1 hour. The infusion can be repeated within 24 hours. Thus, a mammal can receive about 1 to about 5 infusions per day. Preferably, the number of infusions per day is 1 or 2. The period between each infusion can be 1, 2, 3, 4, 5, 6, 7, 8, 9, 10, 11, 12 hours or more. Alternatively, the infusions can be given one after another without a substantial period in between. In one embodiment, the infusion lasts about 45 minutes. The dose may be repeated 2-3 times a week depending on the severity of the relative or absolute deficits of nutrients in the patient. A clinical assessment may be necessary in order to establish the status, but can be limited to a review of medical history, subjective review of symptoms, the subjective opinion of the mammal when human or review of any specific deficits.

Systemic formulations include those designed for administration by injection, e.g., subcutaneous, intravenous, intramuscular, intrathecal or intraperitoneal injection. Useful injectable preparations include sterile suspensions, solutions or emulsions of the active compound(s) in aqueous or oily vehicles. The compositions also can contain solubilizing agents, formulating agents, such as suspending, stabilizing and/or dispersing agent. The formulations for injection can be presented in unit dosage form, e.g., in ampules or in multi-dose containers, and can contain added preservatives. For prophylactic administration, the compound can be administered to a patient at risk of developing one of the previously described conditions or diseases. Alternatively, prophylactic administration can be applied to avoid the onset of symptoms in a patient suffering from or formally diagnosed with the underlying condition.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art coupled with the general and specific examples disclosed herein.

Oral administration of an MDSS composition can be accomplished using dosage forms including, but not limited to, capsules, caplets, solutions, suspensions and/or syrups. Such dosage forms are prepared using conventional methods known to those in the field of pharmaceutical formulation and described in the pertinent texts, e.g., in *Remington: The Science and Practice of Pharmacy* (2000), supra.

The dosage form may be a capsule, in which case the active agent-containing composition may be encapsulated in the form of a liquid. Suitable capsules may be either hard or soft, and are generally made of gelatin, starch, or a cellulosic material, with gelatin capsules preferred. Two-piece hard gelatin capsules are preferably sealed, such as with gelatin bands or the like. See, for e.g., *Remington: The Science and Practice of Pharmacy* (2000), supra, which describes materials and methods for preparing encapsulated pharmaceuticals.

Capsules may, if desired, be coated so as to provide for delayed release. Dosage forms with delayed release coatings may be manufactured using standard coating procedures and equipment. Such procedures are known to those skilled in the art and described in the pertinent texts (see, for e.g., *Remington: The Science and Practice of Pharmacy* (2000), supra). Generally, after preparation of the capsule, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof.

Sustained-release dosage forms provide for drug release over an extended time period, and may or may not be delayed release. Generally, as will be appreciated by those of ordinary skill in the art, sustained-release dosage forms are formulated by dispersing a drug within a matrix of a gradually bioerodible (hydrolyzable) material such as an insoluble plastic, a hydrophilic polymer, or a fatty compound. Insoluble plastic matrices may be comprised of, for example, polyvinyl chloride or polyethylene. Hydrophilic polymers useful for providing a sustained release coating or matrix cellulosic polymers include, without limitation: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit RS) preferred; vinyl polymers and copolymers such as polyvinyl pyrrolidone, polyvinyl acetate, polyvinylacetate phthalate, vinylacetate crotonic acid copolymer, and ethylene-vinyl acetate copolymers; zein; and shellac, ammoniated shellac, shellac-acetyl alcohol, and shellac n-butyl stearate. Fatty compounds for use as a sustained release matrix material include, but are not limited to, waxes generally (e.g., carnauba wax) and glyceryl tristearate.

Topical administration of an MDSS composition can be accomplished using any formulation suitable for application to the body surface, and may comprise, for example, an ointment, cream, gel, lotion, solution, paste or the like, and/or may be prepared so as to contain liposomes, micelles, and/or microspheres. Preferred topical formulations herein are ointments, creams, and gels.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in *Remington: The Science and Practice of Pharmacy* (2000), supra, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight (See, e.g., *Remington: The Science and Practice of Pharmacy* (2002), supra).

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels-are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are cross-linked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

Various additives, known to those skilled in the art, may be included in the topical formulations. For example, solubilizers may be used to solubilize certain active agents. For those drugs having an unusually low rate of permeation through the skin or mucosal tissue, it may be desirable to include a permeation enhancer in the formulation; suitable enhancers are as described elsewhere herein.

Transmucosal administration of an MDSS composition can be accomplished using any type of formulation or dosage unit suitable for application to mucosal tissue. For example, an MDSS composition may be administered to the buccal mucosa in an adhesive patch, sublingually or lingually as a cream, ointment, or paste, nasally as droplets or a nasal spray, or by inhalation of an aerosol formulation or a non-aerosol liquid formulation.

Preferred buccal dosage forms will typically comprise a therapeutically effective amount of an MDSS composition and a bioerodible (hydrolyzable) polymeric carrier that may also serve to adhere the dosage form to the buccal mucosa. The buccal dosage unit is fabricated so as to erode over a predetermined time period, wherein drug delivery is provided essentially throughout. The time period is typically in the range of from about 1 hour to about 72 hours. Preferred buccal delivery preferably occurs over a time period of from about 2 hours to about 24 hours. Buccal drug delivery for short-term use should preferably occur over a time period of from about 2 hours to about 8 hours, more preferably over a time period of from about 3 hours to about 4 hours. As needed buccal drug delivery preferably will occur over a time period of from about 1 hour to about 12 hours, more preferably from about 2 hours to about 8 hours, most preferably from about 3 hours to about 6 hours. Sustained buccal drug delivery will preferably occur over a time period of from about 6 hours to about 72 hours, more preferably from about 12 hours to about 48 hours, most preferably from about 24 hours to about 48 hours. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver.

The "therapeutically effective amount" of an MDSS composition in the buccal dosage unit will of course depend on the potency of an MDSS composition and the intended dosage, which, in turn, is dependent on the particular individual undergoing treatment, the specific indication, and the like. The buccal dosage unit will generally contain from about 1.0 wt. % to about 60 wt. % active agent, preferably on the order of from about 1 wt. % to about 30 wt. % active agent. With regard to the bioerodible (hydrolyzable) polymeric carrier, it will be appreciated that virtually any such carrier can be used, so long as the desired drug release profile is not compromised, and the carrier is compatible with an MDSS composition and any other components of the buccal dosage unit. Generally, the polymeric carrier comprises a hydrophilic (water-soluble and water-swellable) polymer that adheres to the wet surface of the buccal mucosa. Examples of polymeric carriers useful herein include acrylic acid polymers and co, e.g., those known as "carbomers" (Carbopol®, which may be obtained from B. F. Goodrich, is one such polymer). Other suitable polymers include, but are not limited to: hydrolyzed polyvinylalcohol; polyethylene oxides (e.g., Sentry Polyox® water soluble resins, available from Union Carbide); polyacrylates (e.g., Gantrez®, which may be obtained from GAF); vinyl polymers and copolymers; polyvinylpyrrolidone; dextran; guar gum; pectins; starches; and cellulosic polymers such as hydroxypropyl methylcellulose, (e.g., Methocel®, which may be obtained from the Dow Chemical Company), hydroxypropyl cellulose (e.g., Klucel®, which may also be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methyl cellulose, ethyl cellulose, cellulose acetate phthalate, cellulose acetate butyrate, and the like.

Other components may also be incorporated into the buccal dosage forms described herein. The additional components include, but are not limited to, disintegrants, diluents, binders, lubricants, flavoring, colorants, preservatives, and the like. Examples of disintegrants that may be used include, but are not limited to, cross-linked polyvinylpyrrolidones, such as crospovidone (e.g., Polyplasdone® XL, which may be obtained from GAF), cross-linked carboxylic methylcelluloses, such as croscarmelose (e.g., Ac-di-sol®, which may be obtained from FMC), alginic acid, and sodium carboxymethyl starches (e.g., Explotab®, which may be obtained from Edward Medell Co., Inc.), methylcellulose, agar bentonite and alginic acid. Suitable diluents are those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pak®, which may be obtained from Amstar), calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Particularly preferred lubricants are stearates and stearic acid, and an optimal lubricant is magnesium stearate.

Sublingual and lingual dosage forms include creams, ointments and pastes. The cream, ointment or paste for sublingual or lingual delivery comprises a therapeutically effective amount of the selected active agent and one or more conventional nontoxic carriers suitable for sublingual or lingual drug administration. The sublingual and lingual dosage forms of the present invention can be manufactured using conventional processes. The sublingual and lingual dosage units are fabricated to disintegrate rapidly. The time period for complete disintegration of the dosage unit is typically in the range of from about 10 seconds to about 30 minutes, and optimally is less than 5 minutes.

Other components may also be incorporated into the sublingual and lingual dosage forms described herein. The additional components include, but are not limited to binders, disintegrants, wetting agents, lubricants, and the like. Examples of binders that may be used include water, ethanol, polyvinylpyrrolidone; starch solution gelatin solution, and the like. Suitable disintegrants include dry starch, calcium carbonate, polyoxyethylene sorbitan fatty acid esters, sodium lauryl sulfate, stearic monoglyceride, lactose, and the like. Wetting agents, if used, include glycerin, starches, and the like. Particularly preferred lubricants are stearates and polyethylene glycol. Additional components that may be incorporated into sublingual and lingual dosage forms are known, or will be apparent, to those skilled in this art (See, e.g., *Remington: The Science and Practice of Pharmacy* (2000), supra).

Other preferred compositions for sublingual administration include, for example, a bioadhesive to retain an MDSS composition sublingually; a spray, paint, or swab applied to the tongue; or the like. Increased residence time increases the likelihood that the administered invention can be absorbed by the mucosal tissue.

Transdermal administration of MDSS compositions through the skin or mucosal tissue can be accomplished using conventional transdermal drug delivery systems, wherein the agent is contained within a laminated structure (typically referred to as a transdermal "patch") that serves as a drug delivery device to be affixed to the skin.

Transdermal drug delivery may involve passive diffusion or it may be facilitated using electrotransport, e.g., iontophoresis. In a typical transdermal "patch," the drug composition is contained in a layer, or "reservoir," underlying an upper backing layer. The laminated structure may contain a single reservoir, or it may contain multiple reservoirs. In one type of patch, referred to as a "monolithic" system, the reservoir is comprised of a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like.

Alternatively, the drug-containing reservoir and skin contact adhesive are separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active agent and any other materials that are present, the backing is preferably made of a sheet or film of a flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Transdermal drug delivery systems may in addition contain a skin permeation enhancer. That is, because the inherent permeability of the skin to some drugs may be too low to allow therapeutic levels of the drug to pass through a reasonably sized area of unbroken skin, it is necessary to co-administer a skin permeation enhancer with such drugs. Suitable enhancers are well known in the art and include, for example, those enhancers listed below in transmucosal compositions.

As stated above, the MDSS compositions described herein may include vitamins and vitamers, which is a substance(s) that has vitamin-like activity. Vitamins selected from the group consisting of the water soluble and lipid soluble group, and a combination of two or more thereof may also be added to the pharmaceutical composition. Preferably the pharmaceutical composition includes ascorbic acid. It is envisaged that the ascorbic acid will increase the negative and stabilize the anti-oxidant properties of the formulation. Ascorbic acid is included as a strong anti-oxidant component and to maintain the structural integrity of connective tissue, including epithelial basement membranes and to promote wound healing. It may also play a distinct role as an agent with strong anti-inflammatory actions. The oxidized form of the vitamin has been shown to transfer intracellularly where some of it is reduced within the cell. Deficiencies of other B group and A and E are also protected by this vitamin. The B Group of Vitamins has been shown to be important in human food intake, and plays an important role acting as co-enzymes in cellular metabolism and energy production. The entire B group of vitamins is included in the formulation in order to ensure that all vitamins are present so that any deficiencies may addressed in the patient population to be treated with this product. The B group vitamins are always found together to occur naturally together in foods and are included for this reason. The B group includes: 1) Thiamine (B1), which plays an important role in energy production within the cell, specifically as co-enzyme in metabolism of carbohydrates. At least 24 enzymes are known to use thiamine as a co-enzyme; 2) Riboflavin (B2) in the form of flavin mononucleotide and flavin adenine dinucleotide are part of all dehydrogenase enzymes. Deficiency of this vitamin causes inflammation of the mouth, tongue, dermatitis, defective vision and blood dyscrasias; 3) Niacinamide (B3) is included, as part of the B group of vitamins as deficiency syndromes in clinical pellagra are well known clinical manifestations of deficiencies. The deficiency states of this vitamin are associated with intestinal diseases and alcohol misuse. It also occurs in diabetes mellitus and carcinoid syndrome. The active forms of this vitamin include the nicotinamide dinucleotides NAD and NADP, which are the co-enzymes and co-substrates for numerous dehydrogenases responsible for oxidation-reduction systems within the human cell, which are indispensable for energy production. The formation of nicotinic acid from the administered nicotinamide in the formulation produce nicotinic acid possessing additional actions not shared by nicotinamide, such as inhibition of cholesterol synthesis; 4) Calcium D-Pantothenate (B5), pantothenic acid forms a major part of the molecule of co-enzyme A, which is important in the energy producing metabolic cycles in the mitochondria of all cells. The effect of this vitamin on various disease syndromes has been recognized. Such as its use in neurotoxicity produced by streptomycin and its use in diabetic neuropathy, skin diseases and adynamic ileus; and 5) Pyridoxine (B6) is widely utilized as a co-enzyme in over 40 types of enzymatic reactions. The most important of these are the transamination reactions and the influence of pyridoxine on tryptophane metabolism. Kynureminase which is a the enzyme used to identify pyridoxine deficiencies, loses its activity when pyridoxine is not present and may result in secondary nicotinic acid deficiency as a result of lack of the kynureminase conversion of nicotinic acid from tryptophane.

Cyanocobalamin (B12) is used because of the frequent reports of mal-absorption of cyanocobalamin, caused by poor dietary habits senescence and certain drugs (metformin) used as a hypoglycemic agent in diabetes mellitus. This vitamin is essential for normal erythropoeisis to occur and recent findings have also implicated this vitamin with improvement of neuronal transmission in motor neuron disease.

Vitamin K is a fat soluble vitamin. There are two naturally occurring forms of the vitamin. Vitamin K1 is the dietary Vitamin K and is abundant in green leafy vegetables, whereas vitamin K2 is present in tissues. Vitamin K2 is synthesized by bacteria. It is found mainly in fermented products like fermented soybeans, cheese, curds and to some extent also in meat and meat products (Thijssen, H. H., M. J. Drittij-Reijnders, and M. A. Fischer, 1996, Phylloquinone and menaquinone-4 distribution in rats: synthesis rather than uptake determines menaquinone-4 organ concentrations, J Nutr 126:537-43). Vitamin K2 is found in animals as menaquinone. It is the human activated form of vitamin K and is said to promote the healing of bone fractures. It is essential for the carboxylation of glutamate residues in many calcium binding proteins such as calbindin and osteocalcin. These proteins are involved in calcium uptake and bone mineralization. There is no established daily dosage for vitamin K2 but only for Vitamin K1. A typical therapeutic oral dose for vitamin K2 for osteoporosis is 45 mg/day. Therapeutic dose for cancer patients is 25 mg/day, but usually is in the range of 45 mg/day. Unlike for coagulation, we need much higher levels of vitamin K for complete gamma-carboxylation of osteocalcin. Vitamin K deficiency is associated with reduced hip bone mineral density and increased fracture risk in healthy elderly women. Animal studies have shown that the most potent form of vitamin K is vitamin K2, which was administered to rats at 0.1 mg/kg orally. Vitamin K2, in the form of menaquinone-4, is the most biologically active form. Vitamin K2 is a cofactor of gamma-carboxilase and thus essential for the carboxylation of glutamate residues in many calcium binding proteins such as calbindin and osteocalcin (Shearer, M. J., 1992, Vitamin K metabolism and nutriture, Blood Rev 6:92-104). These proteins are involved in calcium uptake and bone mineralization, hence vitamin K2 is said to promote the healing of bone fractures (Hara, K., Y. Akiyama, T. Nakamura, S. Murota, and I. Morita, 1995, The inhibitory effect of vitamin K2 (menatetrenone) on bone resorption may be related to its side chain, Bone 16:179-84).

Unlike for coagulation, a much higher level of vitamin K is needed for complete gamma-carboxylation of osteocalcin (Booth, S. L., and J. W. Suttie, 1998, Dietary intake and adequacy of vitamin K, J. Nutr 128:785-8). Vitamin K deficiency is associated with reduced hip bone mineral density and increased fracture risk in healthy elderly women. Animal studies have shown that the most potent form of vitamin K is vitamin K2, which was administered to rats at 0.1 mg/kg orally (Akiyama, Y., K. Hara, A. Matsumoto, S. Takahashi, and T. Tajima, 1995, Comparison of intestinal absorption of vitamin K2 (menaquinone) homologues and their effects on blood coagulation in rats with hypoprothrombinaemia, Biochem Pharmacol 49:1801-7). Vitamin K2, in the form of menaquinone-4, is the most biologically active form. It has been extensively studied in the treatment of osteoporosis. In one of these studies, 241 osteoporotic women were given 45 mg/day vitamin K2 and 150 mg elemental calcium. After two years, vitamin K2 was shown to maintain lumbar bone mineral density, significant lower fracture incidence (10% versus 30% in the control group (Shiraki, M., Y. Shiraki, C. Aoki, and M. Miura, 2000, Vitamin K2 (menatetrenone) effectively prevents fractures and sustains lumbar bone mineral density in osteoporosis, J Bone Miner Res 15:515-21).

Vitamin K2, but not K1, may inhibit the calcification of arterial plaque. In 1996, animal studies involving rats found high dose of Vitamin K2 (100 mg/kg body weight daily) inhibited the increase in calcium in both kidneys and aorta induced by megadose of synthetic vitamin D (Seyama, Y., M. Horiuch, M. Hayashi, and Y. Kanke, 1996, Effect of vitamin K2 on experimental calcinosis induced by vitamin D2 in rat soft tissue, Int J Vitam Nutr Res 66:36-8). A similar study was conducted with rabbits. High dose of Vitamin K2 (1-10 mg/kg daily for 10 weeks) inhibited the atherosclerotic plaque progression in the aorta and pulmonary arteries (Kawashima, H., Y. Nakajima, Y. Matubara, J. Nakanowatari, T. Fukuta, S. Mizuno, S. Takahashi, T. Tajima, and T. Nakamura, 1997, Effects of vitamin K2 (menatetrenone) on atherosclerosis and blood coagulation in hypercholesterolemic rabbits, Jpn J Pharmacol 75:135-43). Vitamin K2 was also seen to reduce total cholesterol levels, lipid peroxidation, ester cholesterol deposition in the aorta and factor X activity in plasma compared to the control group. A study involving more than 500 postmenopausal women investigated the relation between vitamin K1 and K2 intake and coronary calcification. Sixty-two percent of the women sampled for the study had coronary calcification. Only Vitamin K2 intake was associated with the trend toward decreasing coronary calcification (Beulens, J. W., M. L. Bots, F. Atsma, M. L. Bartelink, M. Prokop, J. M. Geleijnse, J. C. Witteman, D. E. Grobbee, and Y. T. van der Schouw, 2009, High dietary menaquinone intake is associated with reduced coronary calcification, Atherosclerosis 203:489-93).

Both in vivo and in vitro studies have demonstrated that Vitamin K2 has anticancer effect. A multi-cancer study in Japan was performed to test the effect of Vitamin K2 on MDS and post-MDS acute myeloid leukemia patients. Vitamin K2 dosage ranged from 20-135 mg/day orally or 10-50 mg/day intravenously. Vitamin K2 was effective in reducing blast cell numbers in bone marrow and/or peripheral blood in ~71% of those receiving other medication concomitantly (Takami, A., S, Nakao, Y. Ontachi, H. Yamauchi, and T. Matsuda, 1999, Successful therapy of myelodysplastic syndrome with menatetrenone, a vitamin K2 analog, Int J Hemotol 69:24-6). Another study involving 121 patients with hepatocellular carcinoma undergoing conventional therapy has shown that when patients were given 45 mg/day oral vitamin K2, there was a significant increase in survival (Jancin, B, 2002, Vitamin K cuts hepatocellular CA mortality, Fam Pract News 32). A recent study demonstrated that there is inverse association between vitamin K2 and prostate cancer. Higher intake of vitamin K2 might reduce prostate cancer risk by 35%. The association was stronger with advanced prostate cancer incidents. Interestingly, Vitamin K2 from dairy products had stronger effect compared to other sources of vitamin K2 like meat and meat products (Nimptsch, K., S. Rohrmann, and J. Linseisen. 2008. Dietary intake of vitamin K and risk of prostate cancer in the Heidelberg cohort of the European Prospective Investigation into Cancer and Nutrition (EPIC-Heidelberg), *Am J Clin Nutr* 87:985-92).

Magnesium Chloride is required in relatively large concentrations in normal metabolism. It is recognized that deficiency of magnesium is rare unless it is accompanied by severe losses in other electrolytes such as in vomiting and diarrhea. It is however frequently recognized as deficient in the modern diet with symptoms such as muscle tremors and weakness. This mineral is important in many enzymatic reactions and will stabilize excitable membranes. Administered intravenously, magnesium may produce an anesthetic action and this is indirect evidence of its action on the vascular wall endothelial component to stabilize and normalize the surface of the vascular wail.

Heparin is an anti-thrombotic agent capable of reducing platelet aggregation. It may also play a role in vascular endothelial normalization because heparin is related to chondroiten sulphate, which appears naturally as a constituent in the vascular wall and plays a role in the endothelium, which is not fully understood. It has strong anti-inflammatory actions, which appears to be strongly stimulated in formulations described herein because of the presence of carbonic acid capable of neutralizing the acidic charge of heparin. Heparin is a dextrorotary glycosaminoglycan, consisting in a mixture of various polysacharidic chains, composed of repeated D-glucosamine units and also L-idurcnic acid or D-glucuronic acid. Its molecular weight ranges between 6,000 Daltons to 30,000 Daltons, which will depend on either the obtainment source or the methodology, employed for its isolation. The ability in prolonging the blood clotting time is the most known heparin property. Further to the anti-clotting activity, it also shows enzymatic antiproteolitic activity antithrombin, platelet antilyse, thrombolitic, antiserotonergic, and antihistaminic.

Formulations can comprise one or more anesthetics. Patient discomfort or phlebitis and the like can be managed using anesthetic at the site of injection. If used, the anesthetic can be administered separately or as a component of the composition. One or more anesthetics, if present in the composition, is selected from the group consisting of lignocaine, bupivacaine, dibucaine, procaine, chloroprocaine, prilocalne, mepivacaine, etidocaine, tetracaine, lidocaine and xylocalne, and salts, derivatives or mixtures thereof.

Formulations can comprise other ingredients for the treatment of the organism as a whole. For example, an antioxidant additive and/or pro-oxidant additive can be present. The latter may be an agent that acts as a preventive, while the former may be an agent that acts to treat a specific medical condition.

Kits are described comprising a magnetic dipole stabilized solution for injection. In this embodiment, the solution is provided as a sterile composition in a vial. The vial can preferably be an injection vial with a membrane that is suitable for inserting a syringe to pull the solution from the vial or a soft I.V. infusion bag. The solution can be provided as a concentrated solution to which a diluent is added prior to injection. The diluent can be sterile water. The kit may further comprise a pre-filled container which contains the diluent. In a preferred embodiment, a soft infusion bag is pre-filled with diluent. Alternatively, the magnetic dipole stabilized solution vial can contain a solution that is at a concentration which is suitable for injection without any dilution. Preferably, the solution for injection is isotonic. That is, the solution can contain salt, carbohydrates, such as glucose, $NaHCO_3$ or amino acids, such as glycine, and is isotonic with blood plasma.

In some embodiments, the kits comprise a first vial containing a magnetic dipole stabilized solution and a second vial containing components to be admixed with the solution to prepare a composition for injection. The components are listed above. Preferably, the components and the solution are combined just prior to administration. Preferably, in this embodiment, the kit comprises a first container containing a solution comprising one or more selected from the group consisting of vitamins, salts, acids and vitamers, and mixtures thereof; and a second container containing a magnetic dipole stabilized solution. As described herein, it is preferable that the magnetic dipole stabilized solution is electroactivated water. Additionally, the containers can be vials or bags or a combination of both.

Each kit described herein may further comprise instructions for use. The instructions will, of course, depend upon the kit itself and whether a diluent is to be used or other components to be admixed with the magnetic dipole stabilized solution prior to administration.

According to U.S. Pat. No. 7,588,488, there are three types of electrolyzed water, which can be prepared by electrolysis of water having ions dissolved therein. While not strictly defining, the inventors can generally describe that Type A water is a disinfectant that kills a large variety of bacteria, viruses, molds, and spores within seconds of contact. When negatively charged ions migrate to the anode, the fluid around the anode develops a reduced pH in the approximate range of 1.8 to 4.9 and an ORP in the approximate range of +950 to +1450 millivolts (mV). Type A water can be produced as a continuous stream of clear solution having a pH of 1.8 to 4.9, an ORP of +950 to +1450 mV, and containing 8 to 200 parts per million (ppm) of HOCl. When Type A water comes in contact with organic material its pH increases, its ORP drops, and the HOCl dissipates or gases off, thus returning to ordinary water having a small amount of free chlorine (Cl). So-called Type B water is an effective emulsifier and cleaner having antimicrobial properties. It is capable of saponifying surfaces upon contact. Type B water is an alkaline water stream and can be produced as a continuous stream of clear solution produced around the negative electrode, i.e., cathode, during electrolysis. This Type B water is basic with a pH in the approximate range of 9.1 to 12.2. The ORP of Type B water is in the approximate range of +100 to –980 mV. Type B water also contains sodium hydroxide (NaOH) ions in the approximate range of 8 to 200 ppm. Type B water is effective in emulsifying oils and lipids and leaves no residue. Safety and toxicity tests show that Type B water is nontoxic at a pH of 9.5 to 12.2 and an ORP from –350 to –950 mV. So-called Type C water is essentially a form of stabilized Type A water with a longer shelf life. Type C solution has an ORP in the approximate range of 0 to +900 mV, a pH value in the approximate range of 5.5 to 8.2, and contains HOCl in the approximate range of 8 to 80 ppm.

As described above, the electro-activated solutions with a stable positive or negative oxidation-reduction potential may be prepared by any method known in the art. Preferably, sterile, purified water is electro-activated using an open plate palladium-coated electrode in a ceramic-type housing of a module containing ferrous and non-ferrous alloys capable of imparting a fixed magnetic field of at least 7.5 Gauss over a period of time, generally at least 1.75 minutes, at a particular flow rate, generally at least 0.75 liter/minute. The electro-activated water thus obtained has an initial positive oxidation-reduction potential (ORP). Positively charged anolyte water is a carrier for the species formed during electroactivation. The use of negatively charged catholyte water is also contemplated. The electroactivated solution for injection will preferably have a negative potential from about –990 mV to about –0.0001 mV. The negative potential is prepared by mixing the positively charged anolyte water with other components described herein to prepare the MDSS solution for injection. The MDSS for injection can have an ORP of −70 mV and is preferably aqueous in nature.

The present subject matter is based on the unexpected discovery that the MDSS compositions described herein are useful in treating, ameliorating and preventing many conditions and diseases and symptoms thereof. Without being bound to any theory, it is believed that the compositions improve oxygen delivery to the arteries, veins and cardiac muscle and the transport of anti-oxidants and minerals to the bloodstream by causing changes in the concentration gradient of the cellular membranes which in turn modulate transport of physiological ions, such as sodium and potassium. In addition, it is believed that the MDSS compositions improve membrane permeability and thus increases the rate of transport of the minerals and anti-oxidants in the solution. Furthermore, injection of the compositions into the bloodstream provides for the fast and prompt reaching of high levels of nutrients, anti-oxidants and minerals in the blood. It is believed that as a result of these properties of the MDSS compositions described herein, the compositions are surprisingly effective against a number of conditions and diseases.

The methods of the invention include systemic application of magnetic dipole stabilized solutions (MDSS) containing stabilized oxidative species selected from the group consisting of $H_2O$, $O_2$, $H_2O_2$, $Cl_2O$, $H_3O$, $O_3$ and $ClO_2$ as described herein.

The present invention is further described herein by the following non-limiting examples which further illustrate the invention, and are not intended, nor should they be interpreted to, limit the scope of the invention.

EXAMPLES

1. Method of Preparing Magnetic Dipole Stabilized Solution (MDSS)

The following table describes the preparation of MDSS (also referred to as electroactivated water).

2. Specific Formulations a. In one embodiment, a specific formulation for injection comprises:

|  | Concentration/dose | Comment |
|---|---|---|
| Imidazole HCl | 10 mg | |
| Lidocaine HCl | 200 mg | |
| Calcium Gluconate | 200 mg | |
| Thiamine | 15 mg | |
| Riboflavine | 3 mg | |
| Nicotinamide | 150 mg | |
| Pyridoxine | 7.5 mg | |
| Dexpanthenol | 7.5 mg | |
| Ascorbate Na | 50.0 mg | |
| Dextrose | 5% | Caloric source |
| Benzyl Alcohol | 0.5% | Preservative |
| Tetracycline HCl | 350 mg | |
| Water | 20 ml | | b. In one embodiment, a two-container formulation for injection comprises:

|  | Concentration/dose | Comment |
|---|---|---|
| VIAL 1 | | |
| Lidocaine HCl | 200 mg | |
| Thiamine | 15 mg | |
| Riboflavine | 3 mg | |
| Nicotinamide | 150 mg | |
| Pyridoxine | 7.5 mg | |
| Dexpanthenol | 7.5 mg | |
| Ascorbic acid | 50.0 mg | |
| Calcium gluconate | 0.2 g | |
| Dextrose | 5% | |
| Benzyl Alcohol | 0.5% | |
| Neutral bicarbonate ECA | | ORP 400-700; pH 7.0 |

|  |  |  | Preferred Values |
|---|---|---|---|
| 1. FORMULA | Sodium Chloride USP/EP/BP | | 50 g to 200 g/L |
|  | Sodium Bicarbonate USP/EP/BP | | 20 to 96 g/L |
|  | Water for Injection USP | | 1000 mL |
| 2. PREPARATION | Collect Water for Injection in a suitable, pre-sterilized and depyrogenated glass container. | | |
|  | Add Sodium Chloride and Sodium Bicarbonate (pre-weighed quantities) to the WFI and mix until completely dissolved. Addition of heat may be required at a temperature not exceeding 37° C. | | |
|  | Check concentrations of sodium chloride and sodium bicarbonate | | Limits: NaCl: 50-200 g/L NaHCO$_3$: 20-96 g/L |
|  | Release solution for use in MDS preparation | | |
|  | Prepare fluid path with pre-sterilized components, couplers and tubing. | | |
|  | Check machine set-up to deliver suitable flow-rate | | Limit: 20 mL to 250 mL per minute |
|  | Discard 2 Litres of initial effluent. | | |
|  | Measure oxidation reduction potential (ORP) | | ORP: 450-1500 mV |
|  | Measure solution pH | | pH: 3.20-7.60 |
|  | Determine surface tension | | Limit: 45-66 dynes/cm |
|  | Determine ionic species: HClO, ClO$_2$, O$_3$, O$_2$, HO$_2$ | | Limit: NLT 0.01% |
|  | Collect prepared solvent in pre-sterilized container | | |
| 3. QUALITY CONTROL | Measure oxidation reduction potential (ORP) | | ORP: 450-1500 mV |
|  | Measure solution pH | | pH: 3.20-7.60 |
|  | Determine surface tension | | Limit: 45-66 dynes/cm |
|  | Determine ionic species: HClO, ClO$_2$, O$_3$, O$_2$, HO$_2$ | | Limit: NLT 0.01% |

|  | Concentration/dose | Comment |
|---|---|---|
| VIAL 2 | | |
| Heparin Na | 1000 I.U. | |
| Sodium Bicarbonate | 8.5% | |
| Anolyte + ORP | | Solvent & preservative | c. In one embodiment, a two-container formulation for injection comprises:

Container 1 is a vial, which contains a MDSS as described herein as a multi-component injection including a multivitamin combination with minerals, a single amino acid, amino-acetic acid and a local anaesthetic (lidocaine). Container 2 comprises a carrier solution/solvent system, used for dissolution of the components in a physiological buffer which, when combined with Container 1, stabilizes the components for effective delivery to the biophase. This solvent system is prepared from sterile Water For Injection (WFD, which contains a small amount of carbonic acid, derived from $NaHCO_3$. The solvent carries a strong positive or negative electrical charge, as selected for the application. The charge may be monitored by accurate oxidation potential measurements to be at least 800 milli Volts. During dissolution and filling of the injection, the charge may be diminished to about −400 to about −700 milli volts and during storage and shelf life may diminish further to about −70 milli Volts, which is still considered as adequate and effective. The local anaesthetic action is employed to stabilize the membrane of the vascular endothelial cells by blocking of the sodium channels and providing vascular wall relaxation. Both containers are to be diluted before use. The final dose is 200 ml containing 0.9% Sodium Chloride Injection. The final dose can be provided in an infusion bag.

d. In one embodiment, a specific formulation. REV-1 for injection:

|  | Concentration per dose | Comment |
|---|---|---|
| Sodium ascorbate | 395 mg | |
| Magnesium chloride 2 $H_2O$ | 255 mg | |
| 2-di methyl amino ethanol HCl | 200 mg | |
| Thiamine | 36 mg | |
| Riboflavine | 7.3 mg | |
| Nicotinamide | 100 mg | |
| Pyridoxine | 18.2 mg | |
| Calcium pantothenate | 18.2 mg | |
| Cyanocobalamin | 320 µg | |
| ECA water ORP > 800 | 10 ml | Solvent & preservative | e. In one embodiment, a specific formulation for injection comprises:

|  | Formulation Per dose | Total Dose | | Optional ingredients |
|---|---|---|---|---|
| Ascorbic acid | 1000 mg | 1000 mg | | Sodium ascorbate/ Ascorbic acid |
| 2-dimethyl amino ethanol | 300 mg | 300 mg | | 2-dimethyl amino ethanol Aminoacetic acid |
| Ca-d-pantothenate | 2.40 mg | 2.40 mg | | Ca-d-pantothenate |
| Niacinamide | 1100 mg | 1100 mg | | Niacinamide Nicotinic acid |
| Pyridoxine | 1100 mg | 1100 mg | | Pyridoxine |
| Riboflavin | 300 mg | 300 mg | | Riboflavin NAD/co Q10 |
| Thiamine | 60.50 mg | 60.50 mg | | Thiamine |
| Cyanocobalamin | 1500 µg | 1500 µg | | Cyanocobalamin |
| Magnesium sulphate | 0.6 g + 0.4 g | 0.90 g | Vial I + vial II 4.05 mM $Mg^{++}$ | Magnesium sulphate |
| Sodium Bicarbonate | 0.85 g | 0.85 g | Buffer vial II | Sodium Bicarbonate |
| Heparin Na | — | 1000 IU/ml | | Heparin Na |
| MDSS Water | 10 ml | ORP > 900 mV pH 5.5-7.6 | Activator | MDSS Water |
| | | | | Alfa lipoic acid |
| | | | | Vitamin E |
| | | Dose/10 ml | | |
| | | 75 mg | | Phosphatidile serine |
| | | 150 mg | | Glycerophosphatidile choline |
| Ca + Mg | | 200 mg | | Acetyl-L-carnitine |
| Ca-d-pantothenate | 2.40 mg | 1000 mg | | L tyrosine |
| Niacinamide | 1100 mg | 20 mg | | 5 HTP |
| | | 850 mg | | Aspartic acid |
| Pyridoxine | 1100 mg | 0.2 mg | | selenium |
| Riboflavin | 300 mg | 0.1 mg | | copper |
| | | 1 mg | | zinc |
| | | 0.1 mg | | iodine |
| | | 500 mg | | glutathione | f. In one embodiment, a specific formulation for injection comprises:

| Ingredient | Amount Molar |
|---|---|
| Hydrochloride salt of 2-(diethylamino)-N-(2,6-dimethylphenyl) acetamide | 0.055M-0.076M |
| Fructose | 3.5 to 5.5% |
| Nicotinic Acid | 0.95 to 1.25% |
| Thiamine | 0.85 to 1.45% |
| Riboflavin | 0.15 to 0.19% |
| Folic Acid | 0.25 to 0.55% |
| Pyridoxine | 0.15 to 0.19% |
| Ascorbic acid | 2.30 to 2.50% |
| Cyanocobalamin | 0.05 to 0.07% |
| MDSS | to 10 ml. |

All of the above ingredients in this specific formulation are combined into a solution of MDSS that results in a negative electrical potential of preferably about −120 mV to about −20 mV. Most preferably, the potential is about −70 mV. The ingredients are introduced into the vehicle by addition of ascorbic acid followed by the vitamin and carbohydrate constituent. Then, the non-ionized lipid soluble components, previously solubilized in a high speed mixer for about 5 minutes by means of beta cyclodextrin. The ingredients are combined by slow agitation with addition of an inert gas such as nitrogen to the mixture so as to minimize oxidation from taking place. The resultant solution is then transferred to a glass 10 ml vial under an inert atmosphere such as nitrogen. Each vial is then sealed by means of a stopper and an aluminium cap, which is crimped around the seal so as to ensure that the seal is hermetic.

g. In one embodiment, a specific formulation for injection comprises:

| Ingredient | Amount (Molar concentration) |
|---|---|
| Hydrochloride salt of 2-(diethylamino)-N-(2,6-dimethylphenyl) acetamide | 0.055M-0.076 |
| Beta Cyclodextrin hydrate | 0.01-0.05 |
| Hydrochloric acid | to pH 3.2 |
| Nicotinic Acid | 0.95 to 1.25% |
| Thiamine | 0.85 to 1.45% |
| Riboflavin | 0.15 to 0.19% |
| Folic Acid | 0.25 to 0.55% |
| Pyridoxine | 0.15 to 0.19% |
| Ascorbic acid | 2.30 to 2.50% |
| Cyanocobalamin | 0.05 to 0.07% |
| Magnetic Dipole Stabilized Solution | to 10 ml | h. In one embodiment, a specific formulation for injection comprises:

| Ingredient | Amount Molar concentration |
|---|---|
| Hydrochloride salt of 2-(diethylamino)-N-(2,6-dimethylphenyl) acetamide | 0.055M-0.076M |
| Betacyclodextrin hydrate | 0.01-0.50 mg |
| Sodium Chloride | 380-450 mg |
| Phosphate buffer | to pH 7.0 |
| Nicotinic Acid | 0.95 to 1.25% |
| Thiamine | 0.85 to 1.45% |
| Riboflavin | 0.15 to 0.19% |
| Folic Acid | 0.25 to 0.55% |
| Pyridoxine | 0.15 to 0.19% |
| Ascorbic acid | 2.30 to 2.50% |
| Cyanocobalamin | 0.05 to 0.07% |
| Magnetic Dipole Stabilized Solution to 10 ml | to 10 ml | i. In one embodiment, a specific formulation for injection comprises:

| Ingredient | Amount Molar concentration |
|---|---|
| Hydrochloride salt of 2-(diethylamino)-N-(2,6-dimethylphenyl) acetamide | 0.055M-0.076M |
| Hydroxypropylcyclodextri n | 0.01-0.50 mg |
| Sodium Chloride | 380-450 mg |
| Phosphate buffer | to pH 7.0 |
| Sodium Hydroxide | to pH 7.4 |
| Nicotinic Acid | 0.95 to 1.25% |
| Thiamine | 0.85 to 1.45% |
| Riboflavin | 0.15 to 0.19% |
| Folic Acid | 0.25 to 0.55% |
| Pyridoxine | 0.15 to 0.19% |
| Ascorbic acid | 2.30 to 2.50% |
| Cyanocobalamin | 0.05 to 0.07% |
| Mannitol | 2.5% |
| Magnetic Dipole Stabilized Solution to 10 ml | to 10 ml |

3. Clinical Data a. Effect of the Formulations of the Invention on Different Diseases and Conditions

| Symptom or Condition | Diagnosis | No. of patients | Follow up | Dosage Freq. | Formulation | Std. of Care | Stage | Improvement Score |
|---|---|---|---|---|---|---|---|---|
| General Indications (Cosmetic, chronic fatigue, stress etc.) | Interviews and consultations | 50 or more | Some patients are returning for treatment | 1-2 × per week | REV-1 | N/A | 1 | 2 or better |
| Diabetic ulcer | Consultation | 10 or more | Yes | 14 (1 × week) | Heparin included plus buffered anolyte | Yes | 3 | New growth of toe nail and totally pain free |
| Mid shaft fracture non healing | | | Yes | 12 (1 × week) | Heparin included plus buffered anolyte | Yes | 4 | Able to walk without a crutch within 6 weeks |

-continued

| Symptom or Condition | Diagnosis | No. of patients | Follow up | Dosage Freq. | Formulation | Std. of Care | Stage | Improvement Score |
|---|---|---|---|---|---|---|---|---|
| Heart disease | | | Yes | 12 (3 × week) | REV-1 | Yes | 4 | Chest pains disappeared |
| Coronary artery disease | MRI + ECG | 1 | Yes | 7 | REV-1 | Yes | 3 | Normal heart function |
| Perivascular disease affecting lower limbs | Consultation + scan | 2 | Yes | 27 (1 × week) | Heparin included plus buffered anolyte | Yes | 2 | Patient fully mobile, pain free and able to drive |
| Coronary artery disease | MRI + ECG | 1 | Yes | 14 (1 × week) | REV-1 | Yes | 3 | Heart disease cured after 14 weeks |
| Severe intermittent claudication. | Scan and Doppler | 1 | Yes | 40 (1 × week) (Femoral artery) | Heparin included plus buffered anolyte | Yes | 4 | Fully mobile and able to work after 25 weeks |
| Peri-vascular disease | Scan and Doppler | 1 | Yes | 18 (2 × week) | Heparin included plus buffered anolyte | Yes | 3 | Pain free and wound of previous amputation healed |
| Diabetic with renal insufficiency | Clinical | 1 | Yes | 24 (2 × week) | REV-1 | Yes | 2 | Marked improvement after 12 weeks |
| Painful leg after amputation and fall on patella | Consultation | 1 | Yes | 7 intra-arterial injections | Heparin included plus buffered anolyte | Yes | 3 | Totally pain free and able to wear prosthesis |
| Ulcer on toe | Consultation | 1 | Yes | 17 (1 × week) | Heparin included plus buffered anolyte | Yes | 4 | Fully mobile after 8 weeks and pain free |
| Buergers disease | Consultation | 1 | Yes | 16 (1 × week) | REV-1 | Yes | 4 | Lesions completely healed and pain free |
| Coronary artery disease | MRI + ECG | 1 | Yes | 32 (1 × week) | REV-1 | Yes | 3 (80-year old patient) | VEF from 10% to 51% improvement |
| Small varicose vein ulcer | Consultation | 1 | Yes | 3 (1 × week) | REV-1 | Yes | 2 | Ulcer totally disappeared |
| Intermittent claudication | Scan and Doppler | 1 | Yes | 14 (1 × week) | REV-1 | Yes | 3 | Fully mobile, no cramping |
| Heart disease | MRI + ECG | 1 | Yes | 150 (2 × week) | REV-1 | Yes | 3 | No more chest pains |
| Large ulcer on mid shaft | Consultation | 1 | Yes | 14 (1 × week) | REV-1 | Yes | 4 | Ulcer indicates closure. Had been present for 14 years |
| Arterial & venous circulation disorder | Consultation and Doppler | 1 | Yes | 26 (1 × week) | Heparin included plus buffered anolyte | Yes | 2 | Fully recovered |
| Gangrenous foot | Consultation | 1 | Yes | 40 (2 × week) | Heparin included plus buffered anolyte | Yes | 4 (severe developed gangrene) | Walking fine following partial amputation |
| Severe burns on both legs | Consultation | 1 | Yes | 15 (2 × week) | REV-1 | Yes | 3 | Treated on right leg only - after 10 weeks improvement and no infection |
| Calcium Agatston Score Patients (Study) | Scan, MRI, clinical blood tests | 20 | Yes | 12-18 (1-2 × week) | REV-1 | Yes | 1-3 | See summary report |

| Symptom or Condition | Diagnosis | No. of patients | Follow up | Dosage Freq. | Formulation | Std. of Care | Stage | Improvement Score |
|---|---|---|---|---|---|---|---|---|
| Performance enhancement | Consultation | 1 | Yes | 12 (1 × week) (Ongoing) | REV-1 (+ Vit. C) | Yes | 1 | Improvement in athletic performance and general circulation |
| Hearing loss in one ear | Auditory impairment | 1 | Yes | 12 (1 × week) | REV-1 | Yes | 3 | Dramatic improvement |
| Chronic fatigue and poly-pharmacy user, low iron levels | Consultation | 1 | Yes | 20 (2 × week) (Ongoing) | REV-1 | Yes | 4 | Dramatic improvement in general health including increase in ferritin levels |
| Severe diabetic Type II, heart disease | Very high Agatston score | 1 | Yes | 12 (1 × week) | REV-1 | Yes | 4 | Dramatic and sustained improvement in Calcium score and control of sugar levels |
| Severe diabetic Type II, heart disease - Genetic predisposition | High risk cardiac disease and Diabetes Type II | 1 | Yes (Voluntary) | 80 (2 × week) (Ongoing) | REV-1 | Yes | 3 | Dramatic and sustained improvement in Calcium score and control of sugar levels | b. Treatment and Amelioration of Symptoms of Acne.

Three patients were given 1 or 2 infusions a week of REV-1 for a minimum of ten weeks. The results show:

One patient had an improved acne condition after just the 4th treatment.

One patient had less obvious scarring due to acne.

One patient had improved facial color.

Hydration of the skin improved in two patients. As a result, less moisturizer was needed.

Two patients had less wrinkles during and after treatment.

c. Metal Ion Removal

The following describes the ability of a MDSS composition to remove metal ions. Twenty male and female individuals between the ages of 24 and 63 were randomly selected for the treatment, based on age, physical activity and body mass index (BMI). Subjects with a family history of cardiovascular diseases, diabetes mellitus or cancer were included in the treatment. The individuals were subjected to a complete physical examination, blood and urine analyses, calcium score measurement and radiological examination.

The coronary calcium scan is a test that detects the presence and amount of calcium in a coronary artery and correlates that data to plaque formation. The calcium score was 0 in nine subjects; 1 in one subject; 24 in two subjects; 32 in one subject; 40 in one subject; 42 in one subject; 46 in one subject; 57 in one subject; 155 in one subject; 482 in one subject; and 1668 in one subject. The radiological study performed on the twenty individuals showed that individuals with a calcium score of 0 had no calcified plaques, whereas subjects with a calcium score between 24 and 57 had calcified plaques in the left anterior descending artery (LAD). Subjects with a calcium score of 155 or 482 showed calcification in the right coronary artery (RCA) and left anterior descending artery (LAD). The patient with a calcium score of 1668 showed calcification of the right coronary artery, left main artery, left anterior descending artery (LAD), the diagonal and circumflex arteries.

All subjects had their blood pressure and pulse taken before and after each treatment session and treated with a magnetic dipole stabilized solution which is an electro-activated solution prepared as follows.

An electro-activated aqueous solution is prepared using an open plate palladium-coated electrode in a ceramic-type housing of a module containing ferrous and non-ferrous alloys capable of imparting a fixed magnetic field of at least 7.5 Gauss over a period of time of at least 1.75 minutes at a flow rate of at least 0.75 liter/minute. The electro-activated water thus obtained, which has an initial positive oxidation-reduction potential (ORP) in a range between +700 mV and +900 mV, is then collected in a sterilized, air-free and endotoxin-free vessel and used to prepare Solution A and Solution B. Both solutions are used as a diluent for vitamins, salts and minerals.

1.0 liter of Solution A is prepared by dissolving the following vitamins, salts and minerals:

| | |
|---|---|
| Magnesium Sulphate hexahydrate | 60.2 g/L |
| 2-diethylaminoaceto, xylidide | 30.0 g/L |
| Niacinamide | 9.90 g/L |
| Puridoxin HCl | 9.90 g/L |
| Riboflavin-5-phosphate sodium | 0.19 g/L |
| Thiamin HCl | 6.05 g/L |
| Cyanocobalamin crystalline | 0.18 g/L |
| Electrochemically activated water+ | 007.50 ml |

Ascorbic acid, which is a strong anti-oxidant, is added in a concentration of 88.0 g/L and 95.0 g/L, respectively, to reach a stable, negative ORP in a range between −500 mV and −900 mV.

To prepare Solution B, sodium bicarbonate, sodium chloride, magnesium sulfate and calcium are added to increase ionization and produce a stably charged anti-inflammatory solution. A stabilizer may be also added to the solution in an amount of 0.5% mass/volume to increase conductive ionization and produce a stably charged solution with a stable, positive oxidation-reduction potential in a range between +500 mV and +900 mV. The stabilizer may be mixed into the solution by agitation or a sonicator bath and the solution is immediately sealed to prevent entry of oxygen.

1.0 liter of Solution B is prepared by dissolving the following salts and minerals:

| | |
|---|---|
| Sodium Bicarbonate USP | 86.70 g/L |
| Magnesium Sulphate hexahydrate | 20.2 g/L |
| Electrochemically activated water+ | 998.5 ml |

Both solutions A and B are stable for a period of at least 12 months when stored at 20 degrees-34 degrees Celsius.

Solution A and Solution B are then mixed immediately prior to administration to produce a stable composition with a stable negative oxidation-reduction potential (ORP) in a range between −50 mV and −150 mV, a stable pH between 6.6 and 7.9, and a conductivity in the range between 11 and 14 mS/cm.

The final mixture thus obtained comprises the following ingredients:

| | |
|---|---|
| Magnesium sulfate hexahydrate | 0.5-10% |
| Sodium Bicarbonate | 0.5-10% |
| Ascorbic Acid | 5.0-20% |
| Niacinamide | 0.2-2.0% |
| Pyridoxin HCl | 0.005-0.2% |
| Calcium D Pantothenate | 0.01-2.0% |
| Thiamin HCl | 0.1-1.0% |
| Riboflavin | 0.01-0.1% |
| Cyanocobalamin | 0.001-0.1% |
| Magnetic Dipole Stabilized Water | 5.0-500 ml |
| 2-di-ethylaminoethanol | 1.0-3.0% |

The solution was administered to each subject by intravenous injection in an amount of 100 ml of sterile diluent (0.9% sodium chloride injection) for 35 to 55 minutes once or twice a week for a period ranging from two weeks to two months.

The calcium score was measured in the individuals subjected to the treatment with the electro-activated solution at the end of treatment. Table 3 below shows the calcium score of nine individuals with an initial medium to high calcium score before and after 12 treatment sessions. The data in Table 1 clearly show a positive effect of the treatment on individuals with an initial calcium score of 46 and above.

| Patient | Calcium Score Before Treatment | Calcium Score After 12 Treatment Sessions | Percentage of Increase or Decrease |
|---|---|---|---|
| 1 | 24 | 25 | 4% Increase |
| 2 | 24 | 26 | 8% Increase |
| 3 | 32 | 31 | 3% Decrease |
| 4 | 40 | 42 | 5% Increase |
| 5 | 46 | 29 | 37% Decrease |
| 6 | 57 | 40 | 29% Decrease |
| 7 | 155 | 121 | 22% Decrease |
| 8 | 482 | 441 | 9% Decrease |
| 5 | 1668 | 1539 | 8% Decrease |

The magnetic dipole stabilized solutions described herein are surprisingly effective at removing metal ions. Especially preferred magnetic dipole stabilized solutions for this purpose further comprise lipoic acid in the amounts described elsewhere herein.

d. General Malnutrition

The following describes the ability of a MDSS composition to treat malnutrition symptoms. A dose of one infusion per week containing the REV-1+formulation described above was administered. The trial lasted ten weeks. Subject Data: The subjects had malnutrition problems. Some subjects presented with type II diabetic symptoms. Results: One patient stated feeling very good after treatment. Prior to treatment, skin color of ankles was blue. After treatment, the color is pink. Another patient presented with improved hydration in the eyes (electroactivated water was used as eye drops as well), and increased blood circulation. Another patient reported feeling very good with improvement in blood supply to areas of a hand injury. Another patient reports overall well-being and improvements at the same weight, indicating a positive nutritional effect. Other patients report feeling more energetic. One patient reported feeling more energetic and pain in the heel area had improved.

e. Improved Athletic Performance

The formulation, REV-1 was administered to a subject. The subject received 1 treatment per week up to two weeks prior to the event at which time the subject received two treatments per week until the event. After only four treatments, subject noticed an improved running time for 91 km as compared to time before treatment. In a follow-up trial, the subject was given six treatments one year later and again the subject reported higher energy levels during the race.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A composition comprising the product of mixing contents of a first vial with contents of a second vial in a 1:1 ratio,
   the first vial containing an aqueous solution comprising water for injection (WFI), ascorbic acid, thiamine HCl, magnesium sulfate, cyanocobalamin, a B-vitamin, pyridoxine HCl, riboflavin-5'-phosphate, calcium D-pantothenate, and sodium chloride;

the second vial containing an aqueous solution comprising water for injection (WFI) sodium bicarbonate, and sodium chloride, wherein at least one of the aqueous solution in at least one of the first vial or the second vial further comprises an antibiotic, the aqueous solution in the first vial has an electrical potential of +1000 to +1300 prior to mixing, and the aqueous solution in the second vial has an electrical potential of +5 to +700 prior to mixing, wherein the composition has an electrical potential of −1 to +200 and 4.047% to 4.947% by weight of the ascorbic acid, 0.285% to 0.349% by weight pf the thiamine HCl, 3.636% to 4.444% by weight of the magnesium sulfate, 0.0085% to 0.011% by weight of the cyanobalamin, 0.5345% to 0.6535% by weight of the B-vitamin, 0.5345% to 0.6535% by weight of the pyridoxine HCl, 0.012% to 0.014% by weight of the riboflavin 5'-phosphate, 0.013% to 0.016% by weight of the calcium D-pantothenate, 2.10% to 6.30% by weight of the sodium bicarbonate, 0.0009% to 0.0011% by weight of the sodium chloride, and the antibiotic after mixing.

2. The composition of claim 1, wherein the B-vitamin is a form of vitamin B3.

3. The composition of claim 2, wherein the form of vitamin B3 is niacinamide.

4. The composition of claim 1, wherein concentrations in the first vial are 8.9933% by weight ascorbic acid, 0.6333% by weight thiamine HCl, 8.080% by weight magnesium sulfate, 0.0193% by weight cyanocobalamin, 1.188% by weight of niacinamide, 1.188% by weight pyridoxine HCl, 0.0253% by weight riboflavin-5'-phosphate, 0.0293% by weight calcium D-pantothenate, and 0.001% sodium chloride, and concentrations in the second are 8.40% by weight sodium bicarbonate, and 0.001% by weight sodium chloride.

5. A method of treating or ameliorating a skin condition, a condition associated with diabetes, a condition associated with a cardiovascular dysfunction, a cancer, an infection, symptoms of menopause, or metal poisoning in a subject in need thereof, or reducing the amount of metal in a subject in need thereof, or increasing metal excretion from a subject in need thereof, or enhancing performance of a subject or providing nutrition support to a subject in need thereof, comprising administering to a subject in need thereof the composition of claim 1 by injection administration.

* * * * *